United States Patent [19]

Matsui et al.

[11] Patent Number: 5,538,882
[45] Date of Patent: Jul. 23, 1996

[54] VARIANT-TYPE CARBOHYDRATE HYDROLASE, VARIANT GENE OF THE ENZYME AND METHOD FOR PRODUCING OLIGOSACCHARIDE USING THE ENZYME

[75] Inventors: Ikuo Matsui, Tsukuba, Japan; Kazuhiko Ishikawa, Ottawa, Canada; Sachio Miyairi, Tsukuba, Japan; Koichi Honda, Tsukuba, Japan

[73] Assignee: Director-General of Agency of Industrial Science and Techology, Tokyo, Japan

[21] Appl. No.: 204,656

[22] Filed: Mar. 2, 1994

[30] Foreign Application Priority Data

Mar. 4, 1993 [JP] Japan .................................... 5-069303

[51] Int. Cl.⁶ .............................. C12N 9/10; C12N 9/30; C12N 15/54; C12N 15/56
[52] U.S. Cl. ...................... 435/193; 435/202; 435/203; 435/172.3; 435/252.33; 536/23.2
[58] Field of Search .................................... 435/193, 201, 435/202, 203, 172.3, 204, 252.3, 252.33, 320.1; 536/23.2

[56] References Cited

FOREIGN PATENT DOCUMENTS 4-108386  4/1992  Japan .

OTHER PUBLICATIONS

Matsui, I. et al. *Biochemistry* 33(2): 451–458 (1994).
Nakamura, A. et al. *Biochemistry* 33(33): 9929–9936 (1994).
Matsui, I. et al. *Biochemistry* 31:5232–5236 (1992).

*Primary Examiner*—Robert A. Wax
*Assistant Examiner*—Dian C. Jacobson
*Attorney, Agent, or Firm*—Birch, Stewart, Kolasch & Birch

[57] ABSTRACT

There is disclosed a variant-type carbohydrate hydrolase that has been increased transglycosylation activity by substituting another amino acid residue for the tyrosine residue that is present in the active center of the hydrolase, which hydrolase is an amylase or an enzyme analogous to amylase; a gene or a DNA sequence of the carbohydrate hydrolase with mutation introduced into the base sequence that encodes the tyrosine residue; and a vector or a transformant which comprises the DNA sequence. There is also disclosed a method for producing a variety of oligosaccharides and the like by using the variant-type carbohydrate hydrolase.

10 Claims, 1 Drawing Sheet

FIG. 1

Region 1

| Enzyme Name | EC Number | Sequence |
|---|---|---|
| 1. Sfamy | 3.2.1.1 | 73-N T A Y G Y A Y H G [Y] W M K |
| 2. CGT | 2.4.1.19 | 90-S G V N N T A Y H G [Y] W P R |

Region 2

| Enzyme Name | EC Number | Sequence |
|---|---|---|
| 1. Sfamy | 3.2.1.1 | 93-E N F G T A D D |
| 2. CGT | 2.4.1.19 | 110-A A F G S F T D |

Region 3

| Enzyme Name | EC Number | Sequence |
|---|---|---|
| 1. Sfamy | 3.2.1.1 | 112-D M L L M V D I V T N H Y G S |
| 2. CGT | 2.4.1.19 | 129-N I K V V M D F A P N H T N P |

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 1404 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA"

( i i i ) HYPOTHETICAL: NO ( i v ) ANTI-SENSE: NO ( v i i ) IMMEDIATE SOURCE:
        ( B ) CLONE: Derived from plasmid pSf1 (Agric. Biol. Chem.
            ( 1 9 8 5 ) 49:3089-3092)

( i x ) FEATURE:
        ( A ) NAME/KEY: CDS
        ( B ) LOCATION: 1..1404
        ( D ) OTHER INFORMATION: /note="Nucleotides 1-1404
            correspond to nucleotides 79-1482 in the Saccharomycopsis
            fibuligera '- amylase structural gene"

( x i ) SEQUENCE DESCRIPTION: SEQ ID NO:1:

```
GAA  ACT  AAT  GCT  GAT  AAA  TGG  AGA  TCA  CAG  TCT  ATT  TAT  CAA  ATT  GTC        48
Glu  Thr  Asn  Ala  Asp  Lys  Trp  Arg  Ser  Gln  Ser  Ile  Tyr  Gln  Ile  Val
 1                    5                    10                   15

ACT  GAC  AGA  TTT  GCT  AGA  ACC  GAT  GGT  GAT  ACA  AGT  GCT  TCC  TGT  AAC        96
Thr  Asp  Arg  Phe  Ala  Arg  Thr  Asp  Gly  Asp  Thr  Ser  Ala  Ser  Cys  Asn
                20                   25                   30

ACA  GAA  GAT  AGA  CTT  TAC  TGT  GGT  GGT  TCT  TTC  CAA  GGC  ATC  ATA  AAG       144
Thr  Glu  Asp  Arg  Leu  Tyr  Cys  Gly  Gly  Ser  Phe  Gln  Gly  Ile  Ile  Lys
           35                   40                   45

AAG  TTG  GAT  TAC  ATC  AAA  GAT  ATG  GGC  TTT  ACT  GCT  ATT  TGG  ATT  TCT       192
Lys  Leu  Asp  Tyr  Ile  Lys  Asp  Met  Gly  Phe  Thr  Ala  Ile  Trp  Ile  Ser
      50                   55                   60

CCA  GTT  GTT  GAA  AAC  ATT  CCC  GAT  AAC  ACA  GCA  TAT  GGT  TAT  GCT  TAT       240
Pro  Val  Val  Glu  Asn  Ile  Pro  Asp  Asn  Thr  Ala  Tyr  Gly  Tyr  Ala  Tyr
 65                   70                   75                   80

CAT  GGT  TTC  TGG  ATG  AAG  AAC  ATA  TAC  AAA  ATT  AAT  GAA  AAC  TTT  GGT       288
His  Gly  Phe  Trp  Met  Lys  Asn  Ile  Tyr  Lys  Ile  Asn  Glu  Asn  Phe  Gly
                85                   90                   95
```

| | | | | | | | | | | | | | | | | |
|---|---|---|---|---|---|---|---|---|---|---|---|---|---|---|---|---|
| ACT | GCT | GAT | GAT | TTG | AAG | TCT | TTG | GCA | CAA | GAA | TTG | CAC | GAT | CGT | GAT | 336 |
| Thr | Ala | Asp | Asp | Leu | Lys | Ser | Leu | Ala | Gln | Glu | Leu | His | Asp | Arg | Asp | |
| | | | 100 | | | | 105 | | | | | 110 | | | | |
| ATG | TTG | TTA | ATG | GTG | GAT | ATC | GTT | ACC | AAC | CAT | TAC | GGC | AGT | GAT | GGC | 384 |
| Met | Leu | Leu | Met | Val | Asp | Ile | Val | Thr | Asn | His | Tyr | Gly | Ser | Asp | Gly | |
| | | 115 | | | | | 120 | | | | | 125 | | | | |
| AGT | GGA | GAT | AGT | ATC | GAT | TAC | TCA | GAG | TAC | ACC | CCG | TTC | AAC | GAC | CAA | 432 |
| Ser | Gly | Asp | Ser | Ile | Asp | Tyr | Ser | Glu | Tyr | Thr | Pro | Phe | Asn | Asp | Gln | |
| | 130 | | | | | 135 | | | | | 140 | | | | | |
| AAG | TAC | TTC | CAT | AAC | TAC | TGT | CTT | ATT | TCA | AAC | TAT | GAT | GAC | CAA | GCT | 480 |
| Lys | Tyr | Phe | His | Asn | Tyr | Cys | Leu | Ile | Ser | Asn | Tyr | Asp | Asp | Gln | Ala | |
| 145 | | | | | 150 | | | | | 155 | | | | | 160 | |
| CAG | GTT | CAA | AGT | TGC | TGG | GAA | GGT | GAC | TCT | TCA | GTT | GCA | TTA | CCA | GAT | 528 |
| Gln | Val | Gln | Ser | Cys | Trp | Glu | Gly | Asp | Ser | Ser | Val | Ala | Leu | Pro | Asp | |
| | | | | 165 | | | | | 170 | | | | | 175 | | |
| TTG | AGA | ACG | GAA | GAT | AGC | GAC | GTG | GCC | TCA | GTT | TTC | AAT | TCT | TGG | GTT | 576 |
| Leu | Arg | Thr | Glu | Asp | Ser | Asp | Val | Ala | Ser | Val | Phe | Asn | Ser | Trp | Val | |
| | | | | 180 | | | | | 185 | | | | | 190 | | |
| AAA | GAT | TTT | GTT | GGC | AAT | TAC | TCA | ATT | GAT | GGT | TTA | AGA | ATT | GAT | AGT | 624 |
| Lys | Asp | Phe | Val | Gly | Asn | Tyr | Ser | Ile | Asp | Gly | Leu | Arg | Ile | Asp | Ser | |
| | | | 195 | | | | | 200 | | | | | 205 | | | |
| GCT | AAA | CAT | GTG | GAC | CAA | GGC | TTT | TTC | CCG | GAT | TTT | GTT | AGT | CCA | TCT | 672 |
| Ala | Lys | His | Val | Asp | Gln | Gly | Phe | Phe | Pro | Asp | Phe | Val | Ser | Pro | Ser | |
| | 210 | | | | | 215 | | | | | 220 | | | | | |
| GGA | GTT | TAC | TCA | GTA | GGC | GAA | GTT | TTC | CAA | GGA | GAC | CCA | GCT | TAT | ACA | 720 |
| Gly | Val | Tyr | Ser | Val | Gly | Glu | Val | Phe | Gln | Gly | Asp | Pro | Ala | Tyr | Thr | |
| 225 | | | | | 230 | | | | | 235 | | | | | 240 | |
| TGC | CCA | TAC | CAA | AAT | TAC | ATT | CCA | GGG | GTT | AGT | AAT | TAT | CCA | TTG | TAC | 768 |
| Cys | Pro | Tyr | Gln | Asn | Tyr | Ile | Pro | Gly | Val | Ser | Asn | Tyr | Pro | Leu | Tyr | |
| | | | | 245 | | | | | 250 | | | | | 255 | | |
| TAC | CCA | ACC | ACG | AGA | TTT | TTT | AAA | ACT | ACT | GAT | TCA | AGT | TCC | AGT | GAG | 816 |
| Tyr | Pro | Thr | Thr | Arg | Phe | Phe | Lys | Thr | Thr | Asp | Ser | Ser | Ser | Ser | Glu | |
| | | | 260 | | | | | 265 | | | | | 270 | | | |
| TTG | ACT | CAA | ATG | ATT | TCA | AGC | GTT | GCT | TCC | AGT | TGT | TCG | GAT | CCA | ACT | 864 |
| Leu | Thr | Gln | Met | Ile | Ser | Ser | Val | Ala | Ser | Ser | Cys | Ser | Asp | Pro | Thr | |
| | | 275 | | | | | 280 | | | | | 285 | | | | |
| TTG | TTG | ACA | AAC | TTT | GTA | GAA | AAT | CAC | GAT | AAT | GAA | AGG | TTC | GCT | TCA | 912 |
| Leu | Leu | Thr | Asn | Phe | Val | Glu | Asn | His | Asp | Asn | Glu | Arg | Phe | Ala | Ser | |
| | 290 | | | | | 295 | | | | | 300 | | | | | |
| ATG | ACC | AGC | GAC | CAA | AGT | TTG | ATT | TCT | AAT | GCT | ATT | GCA | TTT | GTC | CTT | 960 |
| Met | Thr | Ser | Asp | Gln | Ser | Leu | Ile | Ser | Asn | Ala | Ile | Ala | Phe | Val | Leu | |
| 305 | | | | | 310 | | | | | 315 | | | | | 320 | |
| TTG | GGT | GAT | GGT | ATT | CCT | GTC | ATT | TAC | TAT | GGA | CAA | GAA | CAA | GGC | TTG | 1008 |
| Leu | Gly | Asp | Gly | Ile | Pro | Val | Ile | Tyr | Tyr | Gly | Gln | Glu | Gln | Gly | Leu | |
| | | | | 325 | | | | | 330 | | | | | 335 | | |
| AGC | GGA | AAA | AGT | GAC | CCA | AAC | AAC | AGA | GAG | GCC | TTG | TGG | TTA | TCC | GGC | 1056 |
| Ser | Gly | Lys | Ser | Asp | Pro | Asn | Asn | Arg | Glu | Ala | Leu | Trp | Leu | Ser | Gly | |
| | | | 340 | | | | | 345 | | | | | 350 | | | |
| TAC | AAC | AAA | GAG | AGT | GAC | TAT | TAC | AAG | CTC | ATT | GCC | AAA | GCT | AAT | GCT | 1104 |
| Tyr | Asn | Lys | Glu | Ser | Asp | Tyr | Tyr | Lys | Leu | Ile | Ala | Lys | Ala | Asn | Ala | |
| | | 355 | | | | | 360 | | | | | 365 | | | | |
| GCC | AGA | AAC | GCC | GCC | GTT | TAT | CAA | GAC | TCA | AGC | TAT | GCC | ACC | TCG | CAG | 1152 |
| Ala | Arg | Asn | Ala | Ala | Val | Tyr | Gln | Asp | Ser | Ser | Tyr | Ala | Thr | Ser | Gln | |
| | 370 | | | | | 375 | | | | | 380 | | | | | |
| CTT | TCT | GTG | ATC | TTT | TCA | AAT | GAC | CAT | GTT | ATT | GCA | ACA | AAA | AGA | GGC | 1200 |
| Leu | Ser | Val | Ile | Phe | Ser | Asn | Asp | His | Val | Ile | Ala | Thr | Lys | Arg | Gly | |
| 385 | | | | | 390 | | | | | 395 | | | | | 400 | |
| AGC | GTT | GTT | TCT | GTT | TTC | AAC | AAC | CTT | GGT | TCC | AGC | GGT | TCT | TCT | GAT | 1248 |
| Ser | Val | Val | Ser | Val | Phe | Asn | Asn | Leu | Gly | Ser | Ser | Gly | Ser | Ser | Asp | |
| | | | | 405 | | | | | 410 | | | | | 415 | | |

```
GTG ACT ATT TCC AAC ACA GGT TAC AGT TCC GGT GAG GAT TTG GTA GAA    1296
Val Thr Ile Ser Asn Thr Gly Tyr Ser Ser Gly Glu Asp Leu Val Glu
            420                 425                 430

GTT TTG ACA TGC AGT ACT GTT AGC GGC AGC TCT GAC TTA CAA GTT TCT    1344
Val Leu Thr Cys Ser Thr Val Ser Gly Ser Ser Asp Leu Gln Val Ser
            435                 440                 445

ATC CAA GGT GGT CAA CCA CAA ATC TTT GTT CCT GCT AAA TAT GCT TCT    1392
Ile Gln Gly Gly Gln Pro Gln Ile Phe Val Pro Ala Lys Tyr Ala Ser
    450                 455                 460

GAC ATT TGT TCA                                                     1404
Asp Ile Cys Ser
465
```

( 2 ) INFORMATION FOR SEQ ID NO:2:

( i ) SEQUENCE CHARACTERISTICS:
    ( A ) LENGTH: 468 amino acids
    ( B ) TYPE: amino acid
    ( D ) TOPOLOGY: linear ( i i ) MOLECULE TYPE: protein ( x i ) SEQUENCE DESCRIPTION: SEQ ID NO:2:

```
Glu Thr Asn Ala Asp Lys Trp Arg Ser Gln Ser Ile Tyr Gln Ile Val
 1               5                  10                  15

Thr Asp Arg Phe Ala Arg Thr Asp Gly Asp Thr Ser Ala Ser Cys Asn
            20                  25                  30

Thr Glu Asp Arg Leu Tyr Cys Gly Gly Ser Phe Gln Gly Ile Ile Lys
        35                  40                  45

Lys Leu Asp Tyr Ile Lys Asp Met Gly Phe Thr Ala Ile Trp Ile Ser
    50                  55                  60

Pro Val Val Glu Asn Ile Pro Asp Asn Thr Ala Tyr Gly Tyr Ala Tyr
65                  70                  75                  80

His Gly Phe Trp Met Lys Asn Ile Tyr Lys Ile Asn Glu Asn Phe Gly
                85                  90                  95

Thr Ala Asp Asp Leu Lys Ser Leu Ala Gln Glu Leu His Asp Arg Asp
            100                 105                 110

Met Leu Leu Met Val Asp Ile Val Thr Asn His Tyr Gly Ser Asp Gly
        115                 120                 125

Ser Gly Asp Ser Ile Asp Tyr Ser Glu Tyr Thr Pro Phe Asn Asp Gln
    130                 135                 140

Lys Tyr Phe His Asn Tyr Cys Leu Ile Ser Asn Tyr Asp Asp Gln Ala
145                 150                 155                 160

Gln Val Gln Ser Cys Trp Glu Gly Asp Ser Ser Val Ala Leu Pro Asp
                165                 170                 175

Leu Arg Thr Glu Asp Ser Asp Val Ala Ser Val Phe Asn Ser Trp Val
            180                 185                 190

Lys Asp Phe Val Gly Asn Tyr Ser Ile Asp Gly Leu Arg Ile Asp Ser
        195                 200                 205

Ala Lys His Val Asp Gln Gly Phe Phe Pro Asp Phe Val Ser Pro Ser
    210                 215                 220

Gly Val Tyr Ser Val Gly Glu Val Phe Gln Gly Asp Pro Ala Tyr Thr
225                 230                 235                 240

Cys Pro Tyr Gln Asn Tyr Ile Pro Gly Val Ser Asn Tyr Pro Leu Tyr
                245                 250                 255

Tyr Pro Thr Thr Arg Phe Phe Lys Thr Thr Asp Ser Ser Ser Ser Glu
            260                 265                 270

Leu Thr Gln Met Ile Ser Ser Val Ala Ser Ser Cys Ser Asp Pro Thr
```

|  | 275 |  |  |  |  | 280 |  |  |  |  | 285 |  |  |  |
|---|---|---|---|---|---|---|---|---|---|---|---|---|---|---|
| Leu | Leu 290 | Thr | Asn | Phe | Val | Glu 295 | Asn | His | Asp | Asn | Glu 300 | Arg | Phe | Ala | Ser |
| Met 305 | Thr | Ser | Asp | Gln | Ser 310 | Leu | Ile | Ser | Asn | Ala 315 | Ile | Ala | Phe | Val | Leu 320 |
| Leu | Gly | Asp | Gly | Ile 325 | Pro | Val | Ile | Tyr | Tyr 330 | Gly | Gln | Glu | Gln 335 | Gly | Leu |
| Ser | Gly | Lys | Ser 340 | Asp | Pro | Asn | Asn | Arg 345 | Glu | Ala | Leu | Trp | Leu 350 | Ser | Gly |
| Tyr | Asn | Lys 355 | Glu | Ser | Asp | Tyr | Tyr 360 | Lys | Leu | Ile | Ala | Lys 365 | Ala | Asn | Ala |
| Ala | Arg 370 | Asn | Ala | Ala | Val | Tyr 375 | Gln | Asp | Ser | Ser | Tyr 380 | Ala | Thr | Ser | Gln |
| Leu 385 | Ser | Val | Ile | Phe | Ser 390 | Asn | Asp | His | Val | Ile 395 | Ala | Thr | Lys | Arg | Gly 400 |
| Ser | Val | Val | Ser | Val 405 | Phe | Asn | Asn | Leu | Gly 410 | Ser | Ser | Gly | Ser | Ser 415 | Asp |
| Val | Thr | Ile | Ser 420 | Asn | Thr | Gly | Tyr | Ser 425 | Ser | Gly | Glu | Asp | Leu 430 | Val | Glu |
| Val | Leu | Thr 435 | Cys | Ser | Thr | Val | Ser 440 | Gly | Ser | Ser | Asp | Leu 445 | Gln | Val | Ser |
| Ile | Gln 450 | Gly | Gly | Gln | Pro | Gln 455 | Ile | Phe | Val | Pro | Ala 460 | Lys | Tyr | Ala | Ser |
| Asp 465 | Ile | Cys | Ser |  |  |  |  |  |  |  |  |  |  |  |  |

( 2 ) INFORMATION FOR SEQ ID NO:3:

( i ) SEQUENCE CHARACTERISTICS:
        ( A ) LENGTH: 1404 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic nucleic acid"

( i i i ) HYPOTHETICAL: NO ( i v ) ANTI-SENSE: NO ( v i i ) IMMEDIATE SOURCE:
        ( B ) CLONE: Derived from plasmid pSf1 (Agric. Biol. Chem.
            ( 1 9 8 5 ) 49:3089-3092)

( i x ) FEATURE:
        ( A ) NAME/KEY: CDS
        ( B ) LOCATION: 1..1404
        ( D ) OTHER INFORMATION: /note="Nucleotides 1-1404
            correspond to nucleotides 79-1482 in the Saccharomycopsis
            fibuligera '- amylase structural gene"

( x i ) SEQUENCE DESCRIPTION: SEQ ID NO:3:

| GAA | ACT | AAT | GCT | GAT | AAA | TGG | AGA | TCA | CAG | TCT | ATT | TAT | CAA | ATT | GTC | 48 |
| Glu | Thr | Asn | Ala | Asp | Lys | Trp | Arg | Ser | Gln | Ser | Ile | Tyr | Gln | Ile | Val |  |
| 1 |  |  |  | 5 |  |  |  |  | 10 |  |  |  |  | 15 |  |  |
| ACT | GAC | AGA | TTT | GCT | AGA | ACC | GAT | GGT | GAT | ACA | AGT | GCT | TCC | TGT | AAC | 96 |
| Thr | Asp | Arg | Phe | Ala | Arg | Thr | Asp | Gly | Asp | Thr | Ser | Ala | Ser | Cys | Asn |  |
|  |  |  | 20 |  |  |  |  | 25 |  |  |  |  | 30 |  |  |  |
| ACA | GAA | GAT | AGA | CTT | TAC | TGT | GGT | GGT | TCT | TTC | CAA | GGC | ATC | ATA | AAG | 144 |
| Thr | Glu | Asp | Arg | Leu | Tyr | Cys | Gly | Gly | Ser | Phe | Gln | Gly | Ile | Ile | Lys |  |
|  |  | 35 |  |  |  |  | 40 |  |  |  |  | 45 |  |  |  |  |
| AAG | TTG | GAT | TAC | ATC | AAA | GAT | ATG | GGC | TTT | ACT | GCT | ATT | TGG | ATT | TCT | 192 |

|  |  |  |  |  |  |  |  |  |  |  |  |  |  |  |  |
|---|---|---|---|---|---|---|---|---|---|---|---|---|---|---|---|
| Lys | Leu | Asp | Tyr | Ile | Lys | Asp | Met | Gly | Phe | Thr | Ala | Ile | Trp | Ile | Ser |
|  | 50 |  |  |  | 55 |  |  |  |  | 60 |  |  |  |  |  |

| CCA | GTT | GTT | GAA | AAC | ATT | CCC | GAT | AAC | ACA | GCA | TAT | GGT | TAT | GCT | TAT | 240 |
|---|---|---|---|---|---|---|---|---|---|---|---|---|---|---|---|---|
| Pro | Val | Val | Glu | Asn | Ile | Pro | Asp | Asn | Thr | Ala | Tyr | Gly | Tyr | Ala | Tyr |  |
| 65 |  |  |  | 70 |  |  |  |  | 75 |  |  |  |  | 80 |  |  |

| CAT | GGT | TGG | TGG | ATG | AAG | AAC | ATA | TAC | AAA | ATT | AAT | GAA | AAC | TTT | GGT | 288 |
| His | Gly | Trp | Trp | Met | Lys | Asn | Ile | Tyr | Lys | Ile | Asn | Glu | Asn | Phe | Gly |  |
|  |  |  |  | 85 |  |  |  | 90 |  |  |  |  |  | 95 |  |  |

| ACT | GCT | GAT | GAT | TTG | AAG | TCT | TTG | GCA | CAA | GAA | TTG | CAC | GAT | CGT | GAT | 336 |
| Thr | Ala | Asp | Asp | Leu | Lys | Ser | Leu | Ala | Gln | Glu | Leu | His | Asp | Arg | Asp |  |
|  |  |  | 100 |  |  |  |  | 105 |  |  |  | 110 |  |  |  |  |

| ATG | TTG | TTA | ATG | GTG | GAT | ATC | GTT | ACC | AAC | CAT | TAC | GGC | AGT | GAT | GGC | 384 |
| Met | Leu | Leu | Met | Val | Asp | Ile | Val | Thr | Asn | His | Tyr | Gly | Ser | Asp | Gly |  |
|  |  | 115 |  |  |  |  | 120 |  |  |  |  | 125 |  |  |  |  |

| AGT | GGA | GAT | AGT | ATC | GAT | TAC | TCA | GAG | TAC | ACC | CCG | TTC | AAC | GAC | CAA | 432 |
| Ser | Gly | Asp | Ser | Ile | Asp | Tyr | Ser | Glu | Tyr | Thr | Pro | Phe | Asn | Asp | Gln |  |
|  | 130 |  |  |  |  | 135 |  |  |  |  | 140 |  |  |  |  |  |

| AAG | TAC | TTC | CAT | AAC | TAC | TGT | CTT | ATT | TCA | AAC | TAT | GAT | GAC | CAA | GCT | 480 |
| Lys | Tyr | Phe | His | Asn | Tyr | Cys | Leu | Ile | Ser | Asn | Tyr | Asp | Asp | Gln | Ala |  |
| 145 |  |  |  |  | 150 |  |  |  |  | 155 |  |  |  |  | 160 |  |

| CAG | GTT | CAA | AGT | TGC | TGG | GAA | GGT | GAC | TCT | TCA | GTT | GCA | TTA | CCA | GAT | 528 |
| Gln | Val | Gln | Ser | Cys | Trp | Glu | Gly | Asp | Ser | Ser | Val | Ala | Leu | Pro | Asp |  |
|  |  |  |  | 165 |  |  |  |  | 170 |  |  |  |  | 175 |  |  |

| TTG | AGA | ACG | GAA | GAT | AGC | GAC | GTG | GCC | TCA | GTT | TTC | AAT | TCT | TGG | GTT | 576 |
| Leu | Arg | Thr | Glu | Asp | Ser | Asp | Val | Ala | Ser | Val | Phe | Asn | Ser | Trp | Val |  |
|  |  |  | 180 |  |  |  |  | 185 |  |  |  |  | 190 |  |  |  |

| AAA | GAT | TTT | GTT | GGC | AAT | TAC | TCA | ATT | GAT | GGT | TTA | AGA | ATT | GAT | AGT | 624 |
| Lys | Asp | Phe | Val | Gly | Asn | Tyr | Ser | Ile | Asp | Gly | Leu | Arg | Ile | Asp | Ser |  |
|  |  | 195 |  |  |  |  | 200 |  |  |  |  | 205 |  |  |  |  |

| GCT | AAA | CAT | GTG | GAC | CAA | GGC | TTT | TTC | CCG | GAT | TTT | GTT | AGT | GCA | TCT | 672 |
| Ala | Lys | His | Val | Asp | Gln | Gly | Phe | Phe | Pro | Asp | Phe | Val | Ser | Ala | Ser |  |
|  | 210 |  |  |  |  | 215 |  |  |  |  | 220 |  |  |  |  |  |

| GGA | GTT | TAC | TCA | GTA | GGC | GAA | GTT | TTC | CAA | GGA | GAC | CCA | GCT | TAT | ACA | 720 |
| Gly | Val | Tyr | Ser | Val | Gly | Glu | Val | Phe | Gln | Gly | Asp | Pro | Ala | Tyr | Thr |  |
| 225 |  |  |  |  | 230 |  |  |  |  | 235 |  |  |  |  | 240 |  |

| TGC | CCA | TAC | CAA | AAT | TAC | ATT | CCA | GGG | GTT | AGT | AAT | TAT | CCA | TTG | TAC | 768 |
| Cys | Pro | Tyr | Gln | Asn | Tyr | Ile | Pro | Gly | Val | Ser | Asn | Tyr | Pro | Leu | Tyr |  |
|  |  |  |  | 245 |  |  |  |  | 250 |  |  |  |  | 255 |  |  |

| TAC | CCA | ACC | ACG | AGA | TTT | TTT | AAA | ACT | ACT | GAT | TCA | AGT | TCC | AGT | GAG | 816 |
| Tyr | Pro | Thr | Thr | Arg | Phe | Phe | Lys | Thr | Thr | Asp | Ser | Ser | Ser | Ser | Glu |  |
|  |  | 260 |  |  |  |  | 265 |  |  |  |  | 270 |  |  |  |  |

| TTG | ACT | CAA | ATG | ATT | TCA | AGC | GTT | GCT | TCC | AGT | TGT | TCG | GAT | CCA | ACT | 864 |
| Leu | Thr | Gln | Met | Ile | Ser | Ser | Val | Ala | Ser | Ser | Cys | Ser | Asp | Pro | Thr |  |
|  |  | 275 |  |  |  |  | 280 |  |  |  |  | 285 |  |  |  |  |

| TTG | TTG | ACA | AAC | TTT | GTA | GAA | AAT | CAC | GAT | AAT | GAA | AGG | TTC | GCT | TCA | 912 |
| Leu | Leu | Thr | Asn | Phe | Val | Glu | Asn | His | Asp | Asn | Glu | Arg | Phe | Ala | Ser |  |
|  | 290 |  |  |  |  | 295 |  |  |  |  | 300 |  |  |  |  |  |

| ATG | ACC | AGC | GAC | CAA | AGT | TTG | ATT | TCT | AAT | GCT | ATT | GCA | TTT | GTC | CTT | 960 |
| Met | Thr | Ser | Asp | Gln | Ser | Leu | Ile | Ser | Asn | Ala | Ile | Ala | Phe | Val | Leu |  |
| 305 |  |  |  |  | 310 |  |  |  |  | 315 |  |  |  |  | 320 |  |

| TTG | GGT | GAT | GGT | ATT | CCT | GTC | ATT | TAC | TAT | GGA | CAA | GAA | CAA | GGC | TTG | 1008 |
| Leu | Gly | Asp | Gly | Ile | Pro | Val | Ile | Tyr | Tyr | Gly | Gln | Glu | Gln | Gly | Leu |  |
|  |  |  |  | 325 |  |  |  |  | 330 |  |  |  |  | 335 |  |  |

| AGC | GGA | AAA | AGT | GAC | CCA | AAC | AAC | AGA | GAG | GCC | TTG | TGG | TTA | TCC | GGC | 1056 |
| Ser | Gly | Lys | Ser | Asp | Pro | Asn | Asn | Arg | Glu | Ala | Leu | Trp | Leu | Ser | Gly |  |
|  |  |  | 340 |  |  |  |  | 345 |  |  |  |  | 350 |  |  |  |

| TAC | AAC | AAA | GAG | AGT | GAC | TAT | TAC | AAG | CTC | ATT | GCC | AAA | GCT | AAT | GCT | 1104 |
| Tyr | Asn | Lys | Glu | Ser | Asp | Tyr | Tyr | Lys | Leu | Ile | Ala | Lys | Ala | Asn | Ala |  |
|  |  | 355 |  |  |  |  | 360 |  |  |  |  | 365 |  |  |  |  |

| GCC | AGA | AAC | GCC | GCC | GTT | TAT | CAA | GAC | TCA | AGC | TAT | GCC | ACC | TCG | CAG | 1152 |

```
Ala  Arg  Asn  Ala  Ala  Val  Tyr  Gln  Asp  Ser  Ser  Tyr  Ala  Thr  Ser  Gln
     370                 375                      380

CTT  TCT  GTG  ATC  TTT  TCA  AAT  GAC  CAT  GTT  ATT  GCA  ACA  AAA  AGA  GGC    1200
Leu  Ser  Val  Ile  Phe  Ser  Asn  Asp  His  Val  Ile  Ala  Thr  Lys  Arg  Gly
385                      390                 395                      400

AGC  GTT  GTT  TCT  GTT  TTC  AAC  AAC  CTT  GGT  TCC  AGC  GGT  TCT  TCT  GAT    1248
Ser  Val  Val  Ser  Val  Phe  Asn  Asn  Leu  Gly  Ser  Ser  Gly  Ser  Ser  Asp
               405                      410                      415

GTG  ACT  ATT  TCC  AAC  ACA  GGT  TAC  AGT  TCC  GGT  GAG  GAT  TTG  GTA  GAA    1296
Val  Thr  Ile  Ser  Asn  Thr  Gly  Tyr  Ser  Ser  Gly  Glu  Asp  Leu  Val  Glu
               420                 425                      430

GTT  TTG  ACA  TGC  AGT  ACT  GTT  AGC  GGC  AGC  TCT  GAC  TTA  CAA  GTT  TCT    1344
Val  Leu  Thr  Cys  Ser  Thr  Val  Ser  Gly  Ser  Ser  Asp  Leu  Gln  Val  Ser
          435                      440                      445

ATC  CAA  GGT  GGT  CAA  CCA  CAA  ATC  TTT  GTT  CCT  GCT  AAA  TAT  GCT  TCT    1392
Ile  Gln  Gly  Gly  Gln  Pro  Gln  Ile  Phe  Val  Pro  Ala  Lys  Tyr  Ala  Ser
     450                 455                      460

GAC  ATT  TGT  TCA                                                                 1404
Asp  Ile  Cys  Ser
465
```

( 2 ) INFORMATION FOR SEQ ID NO:4:

( i ) SEQUENCE CHARACTERISTICS:
        ( A ) LENGTH: 468 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Glu  Thr  Asn  Ala  Asp  Lys  Trp  Arg  Ser  Gln  Ser  Ile  Tyr  Gln  Ile  Val
 1                  5                    10                      15

Thr  Asp  Arg  Phe  Ala  Arg  Thr  Asp  Gly  Asp  Thr  Ser  Ala  Ser  Cys  Asn
               20                    25                      30

Thr  Glu  Asp  Arg  Leu  Tyr  Cys  Gly  Gly  Ser  Phe  Gln  Gly  Ile  Ile  Lys
          35                    40                   45

Lys  Leu  Asp  Tyr  Ile  Lys  Asp  Met  Gly  Phe  Thr  Ala  Ile  Trp  Ile  Ser
     50                    55                      60

Pro  Val  Val  Glu  Asn  Ile  Pro  Asp  Asn  Thr  Ala  Tyr  Gly  Tyr  Ala  Tyr
65                       70                   75                           80

His  Gly  Trp  Trp  Met  Lys  Asn  Ile  Tyr  Lys  Ile  Asn  Glu  Asn  Phe  Gly
               85                    90                      95

Thr  Ala  Asp  Asp  Leu  Lys  Ser  Leu  Ala  Gln  Glu  Leu  His  Asp  Arg  Asp
               100                   105                     110

Met  Leu  Leu  Met  Val  Asp  Ile  Val  Thr  Asn  His  Tyr  Gly  Ser  Asp  Gly
          115                   120                     125

Ser  Gly  Asp  Ser  Ile  Asp  Tyr  Ser  Glu  Tyr  Thr  Pro  Phe  Asn  Asp  Gln
     130                   135                    140

Lys  Tyr  Phe  His  Asn  Tyr  Cys  Leu  Ile  Ser  Asn  Tyr  Asp  Asp  Gln  Ala
145                      150                    155                         160

Gln  Val  Gln  Ser  Cys  Trp  Glu  Gly  Asp  Ser  Ser  Val  Ala  Leu  Pro  Asp
               165                   170                     175

Leu  Arg  Thr  Glu  Asp  Ser  Asp  Val  Ala  Ser  Val  Phe  Asn  Ser  Trp  Val
               180                   185                     190

Lys  Asp  Phe  Val  Gly  Asn  Tyr  Ser  Ile  Asp  Gly  Leu  Arg  Ile  Asp  Ser
          195                   200                     205

Ala  Lys  His  Val  Asp  Gln  Gly  Phe  Phe  Pro  Asp  Phe  Val  Ser  Ala  Ser
     210                   215                     220
```

```
Gly  Val  Tyr  Ser  Val  Gly  Glu  Val  Phe  Gln  Gly  Asp  Pro  Ala  Tyr  Thr
225                      230                      235                      240

Cys  Pro  Tyr  Gln  Asn  Tyr  Ile  Pro  Gly  Val  Ser  Asn  Tyr  Pro  Leu  Tyr
                    245                      250                      255

Tyr  Pro  Thr  Thr  Arg  Phe  Phe  Lys  Thr  Thr  Asp  Ser  Ser  Ser  Ser  Glu
               260                      265                      270

Leu  Thr  Gln  Met  Ile  Ser  Ser  Val  Ala  Ser  Ser  Cys  Ser  Asp  Pro  Thr
          275                      280                      285

Leu  Leu  Thr  Asn  Phe  Val  Glu  Asn  His  Asp  Asn  Glu  Arg  Phe  Ala  Ser
     290                      295                      300

Met  Thr  Ser  Asp  Gln  Ser  Leu  Ile  Ser  Asn  Ala  Ile  Ala  Phe  Val  Leu
305                      310                      315                      320

Leu  Gly  Asp  Gly  Ile  Pro  Val  Ile  Tyr  Tyr  Gly  Gln  Glu  Gln  Gly  Leu
                    325                      330                      335

Ser  Gly  Lys  Ser  Asp  Pro  Asn  Asn  Arg  Glu  Ala  Leu  Trp  Leu  Ser  Gly
               340                      345                      350

Tyr  Asn  Lys  Glu  Ser  Asp  Tyr  Tyr  Lys  Leu  Ile  Ala  Lys  Ala  Asn  Ala
          355                      360                      365

Ala  Arg  Asn  Ala  Ala  Val  Tyr  Gln  Asp  Ser  Ser  Tyr  Ala  Thr  Ser  Gln
     370                      375                      380

Leu  Ser  Val  Ile  Phe  Ser  Asn  Asp  His  Val  Ile  Ala  Thr  Lys  Arg  Gly
385                      390                      395                      400

Ser  Val  Val  Ser  Val  Phe  Asn  Asn  Leu  Gly  Ser  Ser  Gly  Ser  Ser  Asp
                    405                      410                      415

Val  Thr  Ile  Ser  Asn  Thr  Gly  Tyr  Ser  Ser  Gly  Glu  Asp  Leu  Val  Glu
               420                      425                      430

Val  Leu  Thr  Cys  Ser  Thr  Val  Ser  Gly  Ser  Ser  Asp  Leu  Gln  Val  Ser
          435                      440                      445

Ile  Gln  Gly  Gly  Gln  Pro  Gln  Ile  Phe  Val  Pro  Ala  Lys  Tyr  Ala  Ser
     450                      455                      460

Asp  Ile  Cys  Ser
465
```

( 2 ) INFORMATION FOR SEQ ID NO:5:

( i ) SEQUENCE CHARACTERISTICS:
        ( A ) LENGTH: 1404 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA"

( i i i ) HYPOTHETICAL: NO ( i v ) ANTI-SENSE: NO ( v i i ) IMMEDIATE SOURCE:
        ( B ) CLONE: Derived from plasmid pSf1 (Agric. Biol. Chem.
            ( 1 9 8 5 ) 49:3089-3092)

( i x ) FEATURE:
        ( A ) NAME/KEY: CDS
        ( B ) LOCATION: 1..1404
        ( D ) OTHER INFORMATION: /note="Nucleotides 1-1404
            correspond to nucleotides 79-1482 of the Saccharomycopis
            fibuligera '- amylase structural gene"

( x i ) SEQUENCE DESCRIPTION: SEQ ID NO:5:

```
GAA  ACT  AAT  GCT  GAT  AAA  TGG  AGA  TCA  CAG  TCT  ATT  TAT  CAA  ATT  GTC       4 8
Glu  Thr  Asn  Ala  Asp  Lys  Trp  Arg  Ser  Gln  Ser  Ile  Tyr  Gln  Ile  Val
```

| | 1 | | | | 5 | | | | | 10 | | | | | 15 | | |
|---|---|---|---|---|---|---|---|---|---|---|---|---|---|---|---|---|---|
| ACT | GAC | AGA | TTT | GCT | AGA | ACC | GAT | GGT | GAT | ACA | AGT | GCT | TCC | TGT | AAC | | 96 |
| Thr | Asp | Arg | Phe | Ala | Arg | Thr | Asp | Gly | Asp | Thr | Ser | Ala | Ser | Cys | Asn | | |
| | | | 20 | | | | | 25 | | | | | 30 | | | | |
| ACA | GAA | GAT | AGA | CTT | TAC | TGT | GGT | GGT | TCT | TTC | CAA | GGC | ATC | ATA | AAG | | 144 |
| Thr | Glu | Asp | Arg | Leu | Tyr | Cys | Gly | Gly | Ser | Phe | Gln | Gly | Ile | Ile | Lys | | |
| | | 35 | | | | | 40 | | | | | 45 | | | | | |
| AAG | TTG | GAT | TAC | ATC | AAA | GAT | ATG | GGC | TTT | ACT | GCT | ATT | TGG | ATT | TCT | | 192 |
| Lys | Leu | Asp | Tyr | Ile | Lys | Asp | Met | Gly | Phe | Thr | Ala | Ile | Trp | Ile | Ser | | |
| | 50 | | | | | 55 | | | | | 60 | | | | | | |
| CCA | GTT | GTT | GAA | AAC | ATT | CCC | GAT | AAC | ACA | GCA | TAT | GGT | TAT | GCT | TAT | | 240 |
| Pro | Val | Val | Glu | Asn | Ile | Pro | Asp | Asn | Thr | Ala | Tyr | Gly | Tyr | Ala | Tyr | | |
| 65 | | | | | 70 | | | | | 75 | | | | | 80 | | |
| CAT | GGT | CTC | TGG | ATG | AAG | AAC | ATA | TAC | AAA | ATT | AAT | GAA | AAC | TTT | GGT | | 288 |
| His | Gly | Leu | Trp | Met | Lys | Asn | Ile | Tyr | Lys | Ile | Asn | Glu | Asn | Phe | Gly | | |
| | | | | 85 | | | | | 90 | | | | | 95 | | | |
| ACT | GCT | GAT | GAT | TTG | AAG | TCT | TTG | GCA | CAA | GAA | TTG | CAC | GAT | CGT | GAT | | 336 |
| Thr | Ala | Asp | Asp | Leu | Lys | Ser | Leu | Ala | Gln | Glu | Leu | His | Asp | Arg | Asp | | |
| | | | 100 | | | | | 105 | | | | | 110 | | | | |
| ATG | TTG | TTA | ATG | GTG | GAT | ATC | GTT | ACC | AAC | CAT | TAC | GGC | AGT | GAT | GGC | | 384 |
| Met | Leu | Leu | Met | Val | Asp | Ile | Val | Thr | Asn | His | Tyr | Gly | Ser | Asp | Gly | | |
| | | 115 | | | | | 120 | | | | | 125 | | | | | |
| AGT | GGA | GAT | AGT | ATC | GAT | TAC | TCA | GAG | TAC | ACC | CCG | TTC | AAC | GAC | CAA | | 432 |
| Ser | Gly | Asp | Ser | Ile | Asp | Tyr | Ser | Glu | Tyr | Thr | Pro | Phe | Asn | Asp | Gln | | |
| | 130 | | | | | 135 | | | | | 140 | | | | | | |
| AAG | TAC | TTC | CAT | AAC | TAC | TGT | CTT | ATT | TCA | AAC | TAT | GAT | GAC | CAA | GCT | | 480 |
| Lys | Tyr | Phe | His | Asn | Tyr | Cys | Leu | Ile | Ser | Asn | Tyr | Asp | Asp | Gln | Ala | | |
| 145 | | | | | 150 | | | | | 155 | | | | | 160 | | |
| CAG | GTT | CAA | AGT | TGC | TGG | GAA | GGT | GAC | TCT | TCA | GTT | GCA | TTA | CCA | GAT | | 528 |
| Gln | Val | Gln | Ser | Cys | Trp | Glu | Gly | Asp | Ser | Ser | Val | Ala | Leu | Pro | Asp | | |
| | | | | 165 | | | | | 170 | | | | | 175 | | | |
| TTG | AGA | ACG | GAA | GAT | AGC | GAC | GTG | GCC | TCA | GTT | TTC | AAT | TCT | TGG | GTT | | 576 |
| Leu | Arg | Thr | Glu | Asp | Ser | Asp | Val | Ala | Ser | Val | Phe | Asn | Ser | Trp | Val | | |
| | | | 180 | | | | | 185 | | | | | 190 | | | | |
| AAA | GAT | TTT | GTT | GGC | AAT | TAC | TCA | ATT | GAT | GGT | TTA | AGA | ATT | GAT | AGT | | 624 |
| Lys | Asp | Phe | Val | Gly | Asn | Tyr | Ser | Ile | Asp | Gly | Leu | Arg | Ile | Asp | Ser | | |
| | | 195 | | | | | 200 | | | | | 205 | | | | | |
| GCT | AAA | CAT | GTG | GAC | CAA | GGC | TTT | TTC | CCG | GAT | TTT | GTT | AGT | GCA | TCT | | 672 |
| Ala | Lys | His | Val | Asp | Gln | Gly | Phe | Phe | Pro | Asp | Phe | Val | Ser | Ala | Ser | | |
| | 210 | | | | | 215 | | | | | 220 | | | | | | |
| GGA | GTT | TAC | TCA | GTA | GGC | GAA | GTT | TTC | CAA | GGA | GAC | CCA | GCT | TAT | ACA | | 720 |
| Gly | Val | Tyr | Ser | Val | Gly | Glu | Val | Phe | Gln | Gly | Asp | Pro | Ala | Tyr | Thr | | |
| 225 | | | | | 230 | | | | | 235 | | | | | 240 | | |
| TGC | CCA | TAC | CAA | AAT | TAC | ATT | CCA | GGG | GTT | AGT | AAT | TAT | CCA | TTG | TAC | | 768 |
| Cys | Pro | Tyr | Gln | Asn | Tyr | Ile | Pro | Gly | Val | Ser | Asn | Tyr | Pro | Leu | Tyr | | |
| | | | | 245 | | | | | 250 | | | | | 255 | | | |
| TAC | CCA | ACC | ACG | AGA | TTT | TTT | AAA | ACT | ACT | GAT | TCA | AGT | TCC | AGT | GAG | | 816 |
| Tyr | Pro | Thr | Thr | Arg | Phe | Phe | Lys | Thr | Thr | Asp | Ser | Ser | Ser | Ser | Glu | | |
| | | | 260 | | | | | 265 | | | | | 270 | | | | |
| TTG | ACT | CAA | ATG | ATT | TCA | AGC | GTT | GCT | TCC | AGT | TGT | TCG | GAT | CCA | ACT | | 864 |
| Leu | Thr | Gln | Met | Ile | Ser | Ser | Val | Ala | Ser | Ser | Cys | Ser | Asp | Pro | Thr | | |
| | | 275 | | | | | 280 | | | | | 285 | | | | | |
| TTG | TTG | ACA | AAC | TTT | GTA | GAA | AAT | CAC | GAT | AAT | GAA | AGG | TTC | GCT | TCA | | 912 |
| Leu | Leu | Thr | Asn | Phe | Val | Glu | Asn | His | Asp | Asn | Glu | Arg | Phe | Ala | Ser | | |
| | 290 | | | | | 295 | | | | | 300 | | | | | | |
| ATG | ACC | AGC | GAC | CAA | AGT | TTG | ATT | TCT | AAT | GCT | ATT | GCA | TTT | GTC | CTT | | 960 |
| Met | Thr | Ser | Asp | Gln | Ser | Leu | Ile | Ser | Asn | Ala | Ile | Ala | Phe | Val | Leu | | |
| 305 | | | | | 310 | | | | | 315 | | | | | 320 | | |
| TTG | GGT | GAT | GGT | ATT | CCT | GTC | ATT | TAC | TAT | GGA | CAA | GAA | CAA | GGC | TTG | | 1008 |
| Leu | Gly | Asp | Gly | Ile | Pro | Val | Ile | Tyr | Tyr | Gly | Gln | Glu | Gln | Gly | Leu | | |

|  |  |  |  |  |  |  |  |  |  |  |  |  |  |  |  |  |
|---|---|---|---|---|---|---|---|---|---|---|---|---|---|---|---|---|
| AGC | GGA | AAA | AGT | GAC | CCA | AAC | AAC | AGA | GAG | GCC | TTG | TGG | TTA | TCC | GGC | 1056 |
| Ser | Gly | Lys | Ser | Asp | Pro | Asn | Asn | Arg | Glu | Ala | Leu | Trp | Leu | Ser | Gly |  |
|  |  |  | 340 |  |  |  |  | 345 |  |  |  |  | 350 |  |  |  |
| TAC | AAC | AAA | GAG | AGT | GAC | TAT | TAC | AAG | CTC | ATT | GCC | AAA | GCT | AAT | GCT | 1104 |
| Tyr | Asn | Lys | Glu | Ser | Asp | Tyr | Tyr | Lys | Leu | Ile | Ala | Lys | Ala | Asn | Ala |  |
|  |  | 355 |  |  |  |  | 360 |  |  |  |  | 365 |  |  |  |  |
| GCC | AGA | AAC | GCC | GCC | GTT | TAT | CAA | GAC | TCA | AGC | TAT | GCC | ACC | TCG | CAG | 1152 |
| Ala | Arg | Asn | Ala | Ala | Val | Tyr | Gln | Asp | Ser | Ser | Tyr | Ala | Thr | Ser | Gln |  |
|  | 370 |  |  |  |  | 375 |  |  |  |  | 380 |  |  |  |  |  |
| CTT | TCT | GTG | ATC | TTT | TCA | AAT | GAC | CAT | GTT | ATT | GCA | ACA | AAA | AGA | GGC | 1200 |
| Leu | Ser | Val | Ile | Phe | Ser | Asn | Asp | His | Val | Ile | Ala | Thr | Lys | Arg | Gly |  |
| 385 |  |  |  |  | 390 |  |  |  |  | 395 |  |  |  |  | 400 |  |
| AGC | GTT | GTT | TCT | GTT | TTC | AAC | AAC | CTT | GGT | TCC | AGC | GGT | TCT | TCT | GAT | 1248 |
| Ser | Val | Val | Ser | Val | Phe | Asn | Asn | Leu | Gly | Ser | Ser | Gly | Ser | Ser | Asp |  |
|  |  |  |  | 405 |  |  |  |  | 410 |  |  |  |  | 415 |  |  |
| GTG | ACT | ATT | TCC | AAC | ACA | GGT | TAC | AGT | TCC | GGT | GAG | GAT | TTG | GTA | GAA | 1296 |
| Val | Thr | Ile | Ser | Asn | Thr | Gly | Tyr | Ser | Ser | Gly | Glu | Asp | Leu | Val | Glu |  |
|  |  |  | 420 |  |  |  |  | 425 |  |  |  |  | 430 |  |  |  |
| GTT | TTG | ACA | TGC | AGT | ACT | GTT | AGC | GGC | AGC | TCT | GAC | TTA | CAA | GTT | TCT | 1344 |
| Val | Leu | Thr | Cys | Ser | Thr | Val | Ser | Gly | Ser | Ser | Asp | Leu | Gln | Val | Ser |  |
|  |  | 435 |  |  |  |  | 440 |  |  |  |  | 445 |  |  |  |  |
| ATC | CAA | GGT | GGT | CAA | CCA | CAA | ATC | TTT | GTT | CCT | GCT | AAA | TAT | GCT | TCT | 1392 |
| Ile | Gln | Gly | Gly | Gln | Pro | Gln | Ile | Phe | Val | Pro | Ala | Lys | Tyr | Ala | Ser |  |
|  | 450 |  |  |  |  | 455 |  |  |  |  | 460 |  |  |  |  |  |
| GAC | ATT | TGT | TCA |  |  |  |  |  |  |  |  |  |  |  |  | 1404 |
| Asp | Ile | Cys | Ser |  |  |  |  |  |  |  |  |  |  |  |  |  |
| 465 |  |  |  |  |  |  |  |  |  |  |  |  |  |  |  |  |

( 2 ) INFORMATION FOR SEQ ID NO:6:

( i ) SEQUENCE CHARACTERISTICS:
        ( A ) LENGTH: 468 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

|  |  |  |  |  |  |  |  |  |  |  |  |  |  |  |
|---|---|---|---|---|---|---|---|---|---|---|---|---|---|---|
| Glu | Thr | Asn | Ala | Asp | Lys | Trp | Arg | Ser | Gln | Ser | Ile | Tyr | Gln | Ile | Val |
| 1 |  |  |  | 5 |  |  |  |  | 10 |  |  |  |  | 15 |  |
| Thr | Asp | Arg | Phe | Ala | Arg | Thr | Asp | Gly | Asp | Thr | Ser | Ala | Ser | Cys | Asn |
|  |  |  | 20 |  |  |  |  | 25 |  |  |  |  | 30 |  |  |
| Thr | Glu | Asp | Arg | Leu | Tyr | Cys | Gly | Gly | Ser | Phe | Gln | Gly | Ile | Ile | Lys |
|  |  | 35 |  |  |  |  | 40 |  |  |  |  | 45 |  |  |  |
| Lys | Leu | Asp | Tyr | Ile | Lys | Asp | Met | Gly | Phe | Thr | Ala | Ile | Trp | Ile | Ser |
|  | 50 |  |  |  |  | 55 |  |  |  |  | 60 |  |  |  |  |
| Pro | Val | Val | Glu | Asn | Ile | Pro | Asp | Asn | Thr | Ala | Tyr | Gly | Tyr | Ala | Tyr |
| 65 |  |  |  |  | 70 |  |  |  |  | 75 |  |  |  |  | 80 |
| His | Gly | Leu | Trp | Met | Lys | Asn | Ile | Tyr | Lys | Ile | Asn | Glu | Asn | Phe | Gly |
|  |  |  |  | 85 |  |  |  |  | 90 |  |  |  |  | 95 |  |
| Thr | Ala | Asp | Asp | Leu | Lys | Ser | Leu | Ala | Gln | Glu | Leu | His | Asp | Arg | Asp |
|  |  |  | 100 |  |  |  |  | 105 |  |  |  |  | 110 |  |  |
| Met | Leu | Leu | Met | Val | Asp | Ile | Val | Thr | Asn | His | Tyr | Gly | Ser | Asp | Gly |
|  |  | 115 |  |  |  |  | 120 |  |  |  |  | 125 |  |  |  |
| Ser | Gly | Asp | Ser | Ile | Asp | Tyr | Ser | Glu | Tyr | Thr | Pro | Phe | Asn | Asp | Gln |
|  | 130 |  |  |  |  | 135 |  |  |  |  | 140 |  |  |  |  |
| Lys | Tyr | Phe | His | Asn | Tyr | Cys | Leu | Ile | Ser | Asn | Tyr | Asp | Asp | Gln | Ala |
| 145 |  |  |  |  | 150 |  |  |  |  | 155 |  |  |  |  | 160 |

| | | | | | | | | | | | | | | |
|---|---|---|---|---|---|---|---|---|---|---|---|---|---|---|
| Gln | Val | Gln | Ser | Cys 165 | Trp | Glu | Gly | Asp | Ser 170 | Ser | Val | Ala | Leu | Pro 175 | Asp |
| Leu | Arg | Thr | Glu 180 | Asp | Ser | Asp | Val | Ala 185 | Ser | Val | Phe | Asn | Ser 190 | Trp | Val |
| Lys | Asp | Phe 195 | Val | Gly | Asn | Tyr | Ser 200 | Ile | Asp | Gly | Leu | Arg 205 | Ile | Asp | Ser |
| Ala | Lys 210 | His | Val | Asp | Gln | Gly 215 | Phe | Phe | Pro | Asp | Phe 220 | Val | Ser | Ala | Ser |
| Gly 225 | Val | Tyr | Ser | Val | Gly 230 | Glu | Val | Phe | Gln | Gly 235 | Asp | Pro | Ala | Tyr | Thr 240 |
| Cys | Pro | Tyr | Gln | Asn 245 | Tyr | Ile | Pro | Gly | Val 250 | Ser | Asn | Tyr | Pro | Leu 255 | Tyr |
| Tyr | Pro | Thr | Thr 260 | Arg | Phe | Phe | Lys | Thr 265 | Thr | Asp | Ser | Ser | Ser 270 | Ser | Glu |
| Leu | Thr | Gln 275 | Met | Ile | Ser | Ser | Val 280 | Ala | Ser | Ser | Cys | Ser 285 | Asp | Pro | Thr |
| Leu | Leu 290 | Thr | Asn | Phe | Val | Glu 295 | Asn | His | Asp | Asn | Glu 300 | Arg | Phe | Ala | Ser |
| Met 305 | Thr | Ser | Asp | Gln | Ser 310 | Leu | Ile | Ser | Asn | Ala 315 | Ile | Ala | Phe | Val | Leu 320 |
| Leu | Gly | Asp | Gly | Ile 325 | Pro | Val | Ile | Tyr | Tyr 330 | Gly | Gln | Glu | Gln | Gly 335 | Leu |
| Ser | Gly | Lys | Ser 340 | Asp | Pro | Asn | Asn | Arg 345 | Glu | Ala | Leu | Trp | Leu 350 | Ser | Gly |
| Tyr | Asn | Lys 355 | Glu | Ser | Asp | Tyr | Tyr 360 | Lys | Leu | Ile | Ala | Lys 365 | Ala | Asn | Ala |
| Ala | Arg 370 | Asn | Ala | Ala | Val | Tyr 375 | Gln | Asp | Ser | Ser | Tyr 380 | Ala | Thr | Ser | Gln |
| Leu 385 | Ser | Val | Ile | Phe | Ser 390 | Asn | Asp | His | Val | Ile 395 | Ala | Thr | Lys | Arg | Gly 400 |
| Ser | Val | Val | Ser | Val 405 | Phe | Asn | Asn | Leu | Gly 410 | Ser | Ser | Gly | Ser | Ser 415 | Asp |
| Val | Thr | Ile | Ser 420 | Asn | Thr | Gly | Tyr | Ser 425 | Ser | Gly | Glu | Asp | Leu 430 | Val | Glu |
| Val | Leu | Thr 435 | Cys | Ser | Thr | Val | Ser 440 | Gly | Ser | Ser | Asp | Leu 445 | Gln | Val | Ser |
| Ile | Gln 450 | Gly | Gly | Gln | Pro | Gln 455 | Ile | Phe | Val | Pro | Ala 460 | Lys | Tyr | Ala | Ser |
| Asp 465 | Ile | Cys | Ser | | | | | | | | | | | | |

( 2 ) INFORMATION FOR SEQ ID NO:7:

( i ) SEQUENCE CHARACTERISTICS:
        ( A ) LENGTH: 1404 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA"

( i i i ) HYPOTHETICAL: NO ( i v ) ANTI-SENSE: NO ( v i i ) IMMEDIATE SOURCE:
        ( B ) CLONE: Derived from plasmid pSf'1 (Agric. Biol. Chem.
        ( 1 9 8 5 ) 49:3089-3092)

( i x ) FEATURE:
    ( A ) NAME/KEY: CDS
    ( B ) LOCATION: 1..1404
    ( D ) OTHER INFORMATION: /note="Nucleotides 1-1404 correspond to nucleotides 79-1482 of the Saccharomycopsis fibuligera '- amylase structural gene"

( x i ) SEQUENCE DESCRIPTION: SEQ ID NO:7:

| | | | | | | | | | | | | | | | | |
|---|---|---|---|---|---|---|---|---|---|---|---|---|---|---|---|---|
| GAA | ACT | AAT | GCT | GAT | AAA | TGG | AGA | TCA | CAG | TCT | ATT | TAT | CAA | ATT | GTC | 48 |
| Glu | Thr | Asn | Ala | Asp | Lys | Trp | Arg | Ser | Gln | Ser | Ile | Tyr | Gln | Ile | Val | |
| 1 | | | | 5 | | | | | 10 | | | | | 15 | | |
| ACT | GAC | AGA | TTT | GCT | AGA | ACC | GAT | GGT | GAT | ACA | AGT | GCT | TCC | TGT | AAC | 96 |
| Thr | Asp | Arg | Phe | Ala | Arg | Thr | Asp | Gly | Asp | Thr | Ser | Ala | Ser | Cys | Asn | |
| | | | 20 | | | | | 25 | | | | | 30 | | | |
| ACA | GAA | GAT | AGA | CTT | TAC | TGT | GGT | GGT | TCT | TTC | CAA | GGC | ATC | ATA | AAG | 144 |
| Thr | Glu | Asp | Arg | Leu | Tyr | Cys | Gly | Gly | Ser | Phe | Gln | Gly | Ile | Ile | Lys | |
| | | 35 | | | | | 40 | | | | | 45 | | | | |
| AAG | TTG | GAT | TAC | ATC | AAA | GAT | ATG | GGC | TTT | ACT | GCT | ATT | TGG | ATT | TCT | 192 |
| Lys | Leu | Asp | Tyr | Ile | Lys | Asp | Met | Gly | Phe | Thr | Ala | Ile | Trp | Ile | Ser | |
| | 50 | | | | | 55 | | | | | 60 | | | | | |
| CCA | GTT | GTT | GAA | AAC | ATT | CCC | GAT | AAC | ACA | GCA | TAT | GGT | TAT | GCT | TAT | 240 |
| Pro | Val | Val | Glu | Asn | Ile | Pro | Asp | Asn | Thr | Ala | Tyr | Gly | Tyr | Ala | Tyr | |
| 65 | | | | | 70 | | | | | 75 | | | | | 80 | |
| CAT | GGT | AAC | TGG | ATG | AAG | AAC | ATA | TAC | AAA | ATT | AAT | GAA | AAC | TTT | GGT | 288 |
| His | Gly | Asn | Trp | Met | Lys | Asn | Ile | Tyr | Lys | Ile | Asn | Glu | Asn | Phe | Gly | |
| | | | | 85 | | | | | 90 | | | | | 95 | | |
| ACT | GCT | GAT | GAT | TTG | AAG | TCT | TTG | GCA | CAA | GAA | TTG | CAC | GAT | CGT | GAT | 336 |
| Thr | Ala | Asp | Asp | Leu | Lys | Ser | Leu | Ala | Gln | Glu | Leu | His | Asp | Arg | Asp | |
| | | | 100 | | | | | 105 | | | | | 110 | | | |
| ATG | TTG | TTA | ATG | GTG | GAT | ATC | GTT | ACC | AAC | CAT | TAC | GGC | AGT | GAT | GGC | 384 |
| Met | Leu | Leu | Met | Val | Asp | Ile | Val | Thr | Asn | His | Tyr | Gly | Ser | Asp | Gly | |
| | | 115 | | | | | 120 | | | | | 125 | | | | |
| AGT | GGA | GAT | AGT | ATC | GAT | TAC | TCA | GAG | TAC | ACC | CCG | TTC | AAC | GAC | CAA | 432 |
| Ser | Gly | Asp | Ser | Ile | Asp | Tyr | Ser | Glu | Tyr | Thr | Pro | Phe | Asn | Asp | Gln | |
| | 130 | | | | | 135 | | | | | 140 | | | | | |
| AAG | TAC | TTC | CAT | AAC | TAC | TGT | CTT | ATT | TCA | AAC | TAT | GAT | GAC | CAA | GCT | 480 |
| Lys | Tyr | Phe | His | Asn | Tyr | Cys | Leu | Ile | Ser | Asn | Tyr | Asp | Asp | Gln | Ala | |
| 145 | | | | | 150 | | | | | 155 | | | | | 160 | |
| CAG | GTT | CAA | AGT | TGC | TGG | GAA | GGT | GAC | TCT | TCA | GTT | GCA | TTA | CCA | GAT | 528 |
| Gln | Val | Gln | Ser | Cys | Trp | Glu | Gly | Asp | Ser | Ser | Val | Ala | Leu | Pro | Asp | |
| | | | | 165 | | | | | 170 | | | | | 175 | | |
| TTG | AGA | ACG | GAA | GAT | AGC | GAC | GTG | GCC | TCA | GTT | TTC | AAT | TCT | TGG | GTT | 576 |
| Leu | Arg | Thr | Glu | Asp | Ser | Asp | Val | Ala | Ser | Val | Phe | Asn | Ser | Trp | Val | |
| | | | 180 | | | | | 185 | | | | | 190 | | | |
| AAA | GAT | TTT | GTT | GGC | AAT | TAC | TCA | ATT | GAT | GGT | TTA | AGA | ATT | GAT | AGT | 624 |
| Lys | Asp | Phe | Val | Gly | Asn | Tyr | Ser | Ile | Asp | Gly | Leu | Arg | Ile | Asp | Ser | |
| | | 195 | | | | | 200 | | | | | 205 | | | | |
| GCT | AAA | CAT | GTG | GAC | CAA | GGC | TTT | TTC | CCG | GAT | TTT | GTT | AGT | GCA | TCT | 672 |
| Ala | Lys | His | Val | Asp | Gln | Gly | Phe | Phe | Pro | Asp | Phe | Val | Ser | Ala | Ser | |
| | 210 | | | | | 215 | | | | | 220 | | | | | |
| GGA | GTT | TAC | TCA | GTA | GGC | GAA | GTT | TTC | CAA | GGA | GAC | CCA | GCT | TAT | ACA | 720 |
| Gly | Val | Tyr | Ser | Val | Gly | Glu | Val | Phe | Gln | Gly | Asp | Pro | Ala | Tyr | Thr | |
| 225 | | | | | 230 | | | | | 235 | | | | | 240 | |
| TGC | CCA | TAC | CAA | AAT | TAC | ATT | CCA | GGG | GTT | AGT | AAT | TAT | CCA | TTG | TAC | 768 |
| Cys | Pro | Tyr | Gln | Asn | Tyr | Ile | Pro | Gly | Val | Ser | Asn | Tyr | Pro | Leu | Tyr | |
| | | | | 245 | | | | | 250 | | | | | 255 | | |
| TAC | CCA | ACC | ACG | AGA | TTT | TTT | AAA | ACT | ACT | GAT | TCA | AGT | TCC | AGT | GAG | 816 |
| Tyr | Pro | Thr | Thr | Arg | Phe | Phe | Lys | Thr | Thr | Asp | Ser | Ser | Ser | Ser | Glu | |
| | | | 260 | | | | | 265 | | | | | 270 | | | |
| TTG | ACT | CAA | ATG | ATT | TCA | AGC | GTT | GCT | TCC | AGT | TGT | TCG | GAT | CCA | ACT | 864 |
| Leu | Thr | Gln | Met | Ile | Ser | Ser | Val | Ala | Ser | Ser | Cys | Ser | Asp | Pro | Thr | |
| | | 275 | | | | | 280 | | | | | 285 | | | | |

| | | | | | | | | | | | | | | | | |
|---|---|---|---|---|---|---|---|---|---|---|---|---|---|---|---|---|
| TTG | TTG | ACA | AAC | TTT | GTA | GAA | AAT | CAC | GAT | AAT | GAA | AGG | TTC | GCT | TCA | 912 |
| Leu | Leu | Thr | Asn | Phe | Val | Glu | Asn | His | Asp | Asn | Glu | Arg | Phe | Ala | Ser | |
| 290 | | | | | 295 | | | | | 300 | | | | | | |
| ATG | ACC | AGC | GAC | CAA | AGT | TTG | ATT | TCT | AAT | GCT | ATT | GCA | TTT | GTC | CTT | 960 |
| Met | Thr | Ser | Asp | Gln | Ser | Leu | Ile | Ser | Asn | Ala | Ile | Ala | Phe | Val | Leu | |
| 305 | | | | | 310 | | | | | 315 | | | | | 320 | |
| TTG | GGT | GAT | GGT | ATT | CCT | GTC | ATT | TAC | TAT | GGA | CAA | GAA | CAA | GGC | TTG | 1008 |
| Leu | Gly | Asp | Gly | Ile | Pro | Val | Ile | Tyr | Tyr | Gly | Gln | Glu | Gln | Gly | Leu | |
| | | | | 325 | | | | | 330 | | | | | 335 | | |
| AGC | GGA | AAA | AGT | GAC | CCA | AAC | AAC | AGA | GAG | GCC | TTG | TGG | TTA | TCC | GGC | 1056 |
| Ser | Gly | Lys | Ser | Asp | Pro | Asn | Asn | Arg | Glu | Ala | Leu | Trp | Leu | Ser | Gly | |
| | | | 340 | | | | | 345 | | | | | 350 | | | |
| TAC | AAC | AAA | GAG | AGT | GAC | TAT | TAC | AAG | CTC | ATT | GCC | AAA | GCT | AAT | GCT | 1104 |
| Tyr | Asn | Lys | Glu | Ser | Asp | Tyr | Tyr | Lys | Leu | Ile | Ala | Lys | Ala | Asn | Ala | |
| | | 355 | | | | | 360 | | | | | 365 | | | | |
| GCC | AGA | AAC | GCC | GCC | GTT | TAT | CAA | GAC | TCA | AGC | TAT | GCC | ACC | TCG | CAG | 1152 |
| Ala | Arg | Asn | Ala | Ala | Val | Tyr | Gln | Asp | Ser | Ser | Tyr | Ala | Thr | Ser | Gln | |
| | 370 | | | | | 375 | | | | | 380 | | | | | |
| CTT | TCT | GTG | ATC | TTT | TCA | AAT | GAC | CAT | GTT | ATT | GCA | ACA | AAA | AGA | GGC | 1200 |
| Leu | Ser | Val | Ile | Phe | Ser | Asn | Asp | His | Val | Ile | Ala | Thr | Lys | Arg | Gly | |
| 385 | | | | | 390 | | | | | 395 | | | | | 400 | |
| AGC | GTT | GTT | TCT | GTT | TTC | AAC | AAC | CTT | GGT | TCC | AGC | GGT | TCT | TCT | GAT | 1248 |
| Ser | Val | Val | Ser | Val | Phe | Asn | Asn | Leu | Gly | Ser | Ser | Gly | Ser | Ser | Asp | |
| | | | | 405 | | | | | 410 | | | | | 415 | | |
| GTG | ACT | ATT | TCC | AAC | ACA | GGT | TAC | AGT | TCC | GGT | GAG | GAT | TTG | GTA | GAA | 1296 |
| Val | Thr | Ile | Ser | Asn | Thr | Gly | Tyr | Ser | Ser | Gly | Glu | Asp | Leu | Val | Glu | |
| | | | 420 | | | | | 425 | | | | | 430 | | | |
| GTT | TTG | ACA | TGC | AGT | ACT | GTT | AGC | GGC | AGC | TCT | GAC | TTA | CAA | GTT | TCT | 1344 |
| Val | Leu | Thr | Cys | Ser | Thr | Val | Ser | Gly | Ser | Ser | Asp | Leu | Gln | Val | Ser | |
| | | 435 | | | | | 440 | | | | | 445 | | | | |
| ATC | CAA | GGT | GGT | CAA | CCA | CAA | ATC | TTT | GTT | CCT | GCT | AAA | TAT | GCT | TCT | 1392 |
| Ile | Gln | Gly | Gly | Gln | Pro | Gln | Ile | Phe | Val | Pro | Ala | Lys | Tyr | Ala | Ser | |
| | 450 | | | | | 455 | | | | | 460 | | | | | |
| GAC | ATT | TGT | TCA | | | | | | | | | | | | | 1404 |
| Asp | Ile | Cys | Ser | | | | | | | | | | | | | |
| 465 | | | | | | | | | | | | | | | | |

( 2 ) INFORMATION FOR SEQ ID NO:8:

( i ) SEQUENCE CHARACTERISTICS:
        ( A ) LENGTH: 468 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Glu | Thr | Asn | Ala | Asp | Lys | Trp | Arg | Ser | Gln | Ser | Ile | Tyr | Gln | Ile | Val |
| 1 | | | | 5 | | | | | 10 | | | | | 15 | |
| Thr | Asp | Arg | Phe | Ala | Arg | Thr | Asp | Gly | Asp | Thr | Ser | Ala | Ser | Cys | Asn |
| | | | 20 | | | | | 25 | | | | | 30 | | |
| Thr | Glu | Asp | Arg | Leu | Tyr | Cys | Gly | Gly | Ser | Phe | Gln | Gly | Ile | Ile | Lys |
| | | 35 | | | | | 40 | | | | | 45 | | | |
| Lys | Leu | Asp | Tyr | Ile | Lys | Asp | Met | Gly | Phe | Thr | Ala | Ile | Trp | Ile | Ser |
| | 50 | | | | | 55 | | | | | 60 | | | | |
| Pro | Val | Val | Glu | Asn | Ile | Pro | Asp | Asn | Thr | Ala | Tyr | Gly | Tyr | Ala | Tyr |
| 65 | | | | | 70 | | | | | 75 | | | | | 80 |
| His | Gly | Asn | Trp | Met | Lys | Asn | Ile | Tyr | Lys | Ile | Asn | Glu | Asn | Phe | Gly |
| | | | | 85 | | | | | 90 | | | | | 95 | |
| Thr | Ala | Asp | Asp | Leu | Lys | Ser | Leu | Ala | Gln | Glu | Leu | His | Asp | Arg | Asp |

|     |     |     |     |     | 100 |     |     |     |     | 105 |     |     |     |     | 110 |     |     |     |
| --- | --- | --- | --- | --- | --- | --- | --- | --- | --- | --- | --- | --- | --- | --- | --- | --- | --- | --- |

Met Leu Leu Met Val Asp Ile Val Thr Asn His Tyr Gly Ser Asp Gly
          115                         120                125

Ser Gly Asp Ser Ile Asp Tyr Ser Glu Tyr Thr Pro Phe Asn Asp Gln
    130                 135                 140

Lys Tyr Phe His Asn Tyr Cys Leu Ile Ser Asn Tyr Asp Asp Gln Ala
145             150                 155                         160

Gln Val Gln Ser Cys Trp Glu Gly Asp Ser Ser Val Ala Leu Pro Asp
            165             170                         175

Leu Arg Thr Glu Asp Ser Asp Val Ala Ser Val Phe Asn Ser Trp Val
        180                 185                 190

Lys Asp Phe Val Gly Asn Tyr Ser Ile Asp Gly Leu Arg Ile Asp Ser
        195                 200                 205

Ala Lys His Val Asp Gln Gly Phe Phe Pro Asp Phe Val Ser Ala Ser
    210                 215                 220

Gly Val Tyr Ser Val Gly Glu Val Phe Gln Gly Asp Pro Ala Tyr Thr
225                 230                 235                 240

Cys Pro Tyr Gln Asn Tyr Ile Pro Gly Val Ser Asn Tyr Pro Leu Tyr
                245                 250                 255

Tyr Pro Thr Thr Arg Phe Phe Lys Thr Thr Asp Ser Ser Ser Ser Glu
            260                 265                 270

Leu Thr Gln Met Ile Ser Ser Val Ala Ser Ser Cys Ser Asp Pro Thr
        275                 280                 285

Leu Leu Thr Asn Phe Val Glu Asn His Asp Asn Glu Arg Phe Ala Ser
    290                 295                 300

Met Thr Ser Asp Gln Ser Leu Ile Ser Asn Ala Ile Ala Phe Val Leu
305                 310                 315                 320

Leu Gly Asp Gly Ile Pro Val Ile Tyr Tyr Gly Gln Glu Gln Gly Leu
            325                 330                 335

Ser Gly Lys Ser Asp Pro Asn Asn Arg Glu Ala Leu Trp Leu Ser Gly
            340                 345                 350

Tyr Asn Lys Glu Ser Asp Tyr Tyr Lys Leu Ile Ala Lys Ala Asn Ala
        355                 360                 365

Ala Arg Asn Ala Ala Val Tyr Gln Asp Ser Ser Tyr Ala Thr Ser Gln
    370                 375                 380

Leu Ser Val Ile Phe Ser Asn Asp His Val Ile Ala Thr Lys Arg Gly
385                 390                 395                 400

Ser Val Val Ser Val Phe Asn Asn Leu Gly Ser Ser Gly Ser Ser Asp
            405                 410                 415

Val Thr Ile Ser Asn Thr Gly Tyr Ser Ser Gly Glu Asp Leu Val Glu
        420                 425                 430

Val Leu Thr Cys Ser Thr Val Ser Gly Ser Ser Asp Leu Gln Val Ser
        435                 440                 445

Ile Gln Gly Gly Gln Pro Gln Ile Phe Val Pro Ala Lys Tyr Ala Ser
    450                 455                 460

Asp Ile Cys Ser
465

( 2 ) INFORMATION FOR SEQ ID NO:9:

( i ) SEQUENCE CHARACTERISTICS:
        ( A ) LENGTH: 2061 base pairs
        ( B ) TYPE: nucleic acid
        ( C ) STRANDEDNESS: double
        ( D ) TOPOLOGY: linear 5,538,882

45

46

-continued (ii) MOLECULE TYPE: other nucleic acid
(A) DESCRIPTION: /desc ="Synthetic DNA"

(iii) HYPOTHETICAL: NO (iv) ANTI-SENSE: NO (vii) IMMEDIATE SOURCE:
(A) LIBRARY: Library of chromosomal DNA from Bacillus
macerans, pMAC, generated by treating chromosomal DNA
from Bacillus macerans,IAM1243 with a restriction enzyme, and inserting
and linking restriction fragments to pBR322

(ix) FEATURE:
(A) NAME/KEY: CDS
(B) LOCATION: 1..2061
(D) OTHER INFORMATION: /note="Nucleotides 1-2061
correspond to nucleotides 82- 2142 of the Bacillus macerans
cyclomaltodextrin glucanotransferase structural gene"

(xi) SEQUENCE DESCRIPTION: SEQ ID NO:9:

```
TCA CCC GAT ACG AGC GTG GAC AAC AAG GTC AAT TTC AGT ACG GAC GTC    48
Ser Pro Asp Thr Ser Val Asp Asn Lys Val Asn Phe Ser Thr Asp Val
  1           5                  10                  15

ATC TAT CAG ATT GTG ACC GAC CGC TTC GCG GAC GGG GAC AGG ACG AAC    96
Ile Tyr Gln Ile Val Thr Asp Arg Phe Ala Asp Gly Asp Arg Thr Asn
             20                  25                  30

AAT CCG GCG GGG GAT GCG TTC AGC GGC GAC CGA TCC AAT TTG AAG CTC   144
Asn Pro Ala Gly Asp Ala Phe Ser Gly Asp Arg Ser Asn Leu Lys Leu
         35                  40                  45

TAT TTC GGG GGA GAC TGG CAG GGG ATT ATC GAC AAG ATT AAC GAC GGT   192
Tyr Phe Gly Gly Asp Trp Gln Gly Ile Ile Asp Lys Ile Asn Asp Gly
     50                  55                  60

TAT TTG ACC GGC ATG GGC GTC ACC GCC CTC TGG ATA TCC CAA CCT GTG   240
Tyr Leu Thr Gly Met Gly Val Thr Ala Leu Trp Ile Ser Gln Pro Val
 65                  70                  75                  80

GAA AAT ATC ACC TCC GTC ATC AAG TAT TCC GGC GTT AAC AAT ACG TCT   288
Glu Asn Ile Thr Ser Val Ile Lys Tyr Ser Gly Val Asn Asn Thr Ser
                 85                  90                  95

TAT CAC GGT TGG TGG GCG AGG GAT TTT AAG CAA ACC AAC GAC GCT TTC   336
Tyr His Gly Trp Trp Ala Arg Asp Phe Lys Gln Thr Asn Asp Ala Phe
            100                 105                 110

GGG GAT TTT GCC GAT TTT CAA AAT CTG ATT GAT ACG CTC ACG CTC ATA   384
Gly Asp Phe Ala Asp Phe Gln Asn Leu Ile Asp Thr Leu Thr Leu Ile
        115                 120                 125

ACA TCA AGG TCG GAT CGA CTT CGC CCC CAA CCA CAC GTC TCC GGC CGA   432
Thr Ser Arg Ser Asp Arg Leu Arg Pro Gln Pro His Val Ser Gly Arg
    130                 135                 140

GCA GGG ACG AAC CCC GGC TTC GCC GAG AAC GGT GCG CTG TAT GAT AAC   480
Ala Gly Thr Asn Pro Gly Phe Ala Glu Asn Gly Ala Leu Tyr Asp Asn
145                 150                 155                 160

GGT TCG CTG CTC GGC GCC TAC AGC AAT GAT ACG GCC GGC CTT TTC CAT   528
Gly Ser Leu Leu Gly Ala Tyr Ser Asn Asp Thr Ala Gly Leu Phe His
                165                 170                 175

CAT AAC GGG GGG ACC GAT TTT TCC ACG ATT GAA GAC GGT ATT TAC AAG   576
His Asn Gly Gly Thr Asp Phe Ser Thr Ile Glu Asp Gly Ile Tyr Lys
            180                 185                 190

AAC CTC TAC GAC CTG GCG GAC ATC AAC CAT AAC AAC GCT ATG GAC       624
Asn Leu Tyr Asp Leu Ala Asp Ile Asn His Asn Asn Ala Met Asp
        195                 200                 205

GCT TAT TTT AAA AGC GCT ATC GAC CTT TGG CTC GGC ATG GGT GTG GAC   672
Ala Tyr Phe Lys Ser Ala Ile Asp Leu Trp Leu Gly Met Gly Val Asp
    210                 215                 220

GGG ATT CGT TTT GAC GGG GTG AAG CAG TAT CCT TTC GGC TGG CAA AAA   720
Gly Ile Arg Phe Asp Gly Val Lys Gln Tyr Pro Phe Gly Trp Gln Lys
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| 225 |     |     |     |     | 230 |     |     |     |     | 235 |     |     |     |     | 240 |      |
| AGC | TTC | GTT | TCC | TCG | ATT | TAC | GGC | GGC | GAT | CAT | CCG | GTA | TTT | ACG | TTC | 768  |
| Ser | Phe | Val | Ser | Ser | Ile | Tyr | Gly | Gly | Asp | His | Pro | Val | Phe | Thr | Phe |      |
|     |     |     |     | 245 |     |     |     |     | 250 |     |     |     |     | 255 |     |      |
| GGG | GAA | TGG | TAT | CTT | GGC | GCG | GAT | CAA | ACC | GAC | GGA | GAC | AAC | ATT | AAA | 816  |
| Gly | Glu | Trp | Tyr | Leu | Gly | Ala | Asp | Gln | Thr | Asp | Gly | Asp | Asn | Ile | Lys |      |
|     |     |     | 260 |     |     |     |     | 265 |     |     |     |     | 270 |     |     |      |
| TTC | GCC | AAC | GAA | AGC | GGG | ATG | AAC | CTG | CTG | GAC | TTT | GAA | TAC | GCG | CAG | 864  |
| Phe | Ala | Asn | Glu | Ser | Gly | Met | Asn | Leu | Leu | Asp | Phe | Glu | Tyr | Ala | Gln |      |
|     |     | 275 |     |     |     |     | 280 |     |     |     |     | 285 |     |     |     |      |
| GAA | GTG | CGC | GAA | GTG | TTC | CGG | GAC | AAA | ACG | GAA | ACG | ATG | AAG | GAT | CTC | 912  |
| Glu | Val | Arg | Glu | Val | Phe | Arg | Asp | Lys | Thr | Glu | Thr | Met | Lys | Asp | Leu |      |
|     | 290 |     |     |     |     | 295 |     |     |     |     | 300 |     |     |     |     |      |
| TAT | GAG | GTG | CTG | GCC | AGC | ACG | GAG | TCG | CAA | TAC | GAC | TAC | ATC | AAC | AAT | 960  |
| Tyr | Glu | Val | Leu | Ala | Ser | Thr | Glu | Ser | Gln | Tyr | Asp | Tyr | Ile | Asn | Asn |      |
| 305 |     |     |     |     | 310 |     |     |     |     | 315 |     |     |     |     | 320 |      |
| ATG | GTG | ACC | TTC | ATC | GAC | AAC | CAT | GAT | ATG | GAC | CGG | TTC | CAG | GTT | GCC | 1008 |
| Met | Val | Thr | Phe | Ile | Asp | Asn | His | Asp | Met | Asp | Arg | Phe | Gln | Val | Ala |      |
|     |     |     |     | 325 |     |     |     |     | 330 |     |     |     |     | 335 |     |      |
| GGT | TCC | GGT | ACG | CGG | GCG | ACC | GAG | CAA | GCG | TTG | GCG | CTG | ACG | CTG | ACT | 1056 |
| Gly | Ser | Gly | Thr | Arg | Ala | Thr | Glu | Gln | Ala | Leu | Ala | Leu | Thr | Leu | Thr |      |
|     |     |     | 340 |     |     |     |     | 345 |     |     |     |     | 350 |     |     |      |
| TCC | CGC | GGC | GTG | CCA | GCC | ATC | TAC | TAC | GGC | ACG | GAG | CAG | TAC | ATG | ACC | 1104 |
| Ser | Arg | Gly | Val | Pro | Ala | Ile | Tyr | Tyr | Gly | Thr | Glu | Gln | Tyr | Met | Thr |      |
|     |     | 355 |     |     |     |     | 360 |     |     |     |     | 365 |     |     |     |      |
| GGC | GAT | GGC | GAC | CCC | AAC | AAC | CGG | GCG | ATG | ATG | ACC | TCG | TTT | AAT | ACC | 1152 |
| Gly | Asp | Gly | Asp | Pro | Asn | Asn | Arg | Ala | Met | Met | Thr | Ser | Phe | Asn | Thr |      |
|     | 370 |     |     |     |     | 375 |     |     |     |     | 380 |     |     |     |     |      |
| GGG | ACG | ACG | GCT | TAT | AAA | GTG | ATT | CAG | GCA | TTG | GCG | CCG | CTG | CGT | AAA | 1200 |
| Gly | Thr | Thr | Ala | Tyr | Lys | Val | Ile | Gln | Ala | Leu | Ala | Pro | Leu | Arg | Lys |      |
| 385 |     |     |     |     | 390 |     |     |     |     | 395 |     |     |     |     | 400 |      |
| TCC | AAT | CCG | GCC | ATC | GCT | TAT | GGG | ACG | ACG | ACA | GAG | CGC | TGG | GTT | AAC | 1248 |
| Ser | Asn | Pro | Ala | Ile | Ala | Tyr | Gly | Thr | Thr | Thr | Glu | Arg | Trp | Val | Asn |      |
|     |     |     |     | 405 |     |     |     |     | 410 |     |     |     |     | 415 |     |      |
| AAC | GAT | GTG | TTG | ATT | ATT | GAA | CGC | AAA | TTC | GGC | AGC | AGC | GCC | GCT | TTG | 1296 |
| Asn | Asp | Val | Leu | Ile | Ile | Glu | Arg | Lys | Phe | Gly | Ser | Ser | Ala | Ala | Leu |      |
|     |     |     | 420 |     |     |     |     | 425 |     |     |     |     | 430 |     |     |      |
| GTG | GCG | ATT | AAT | CGA | AAC | TCG | TCC | GCC | GCT | TAT | CCG | ATT | TCG | GGT | CTG | 1344 |
| Val | Ala | Ile | Asn | Arg | Asn | Ser | Ser | Ala | Ala | Tyr | Pro | Ile | Ser | Gly | Leu |      |
|     |     | 435 |     |     |     |     | 440 |     |     |     |     | 445 |     |     |     |      |
| TTG | AGT | TCG | CTG | CCG | GCG | GGC | ACT | TAT | TCG | GAT | GTA | TTG | AAC | GGA | CTC | 1392 |
| Leu | Ser | Ser | Leu | Pro | Ala | Gly | Thr | Tyr | Ser | Asp | Val | Leu | Asn | Gly | Leu |      |
|     | 450 |     |     |     |     | 455 |     |     |     |     | 460 |     |     |     |     |      |
| TTA | AAC | GGC | AAC | TCC | ATT | ACC | GTG | GGC | AGC | GGC | GGC | GCC | GTC | ACC | AAC | 1440 |
| Leu | Asn | Gly | Asn | Ser | Ile | Thr | Val | Gly | Ser | Gly | Gly | Ala | Val | Thr | Asn |      |
| 465 |     |     |     |     | 470 |     |     |     |     | 475 |     |     |     |     | 480 |      |
| TTT | ACG | CTG | GCG | GCC | GGC | GGC | ACG | GCG | GTA | TGG | CAG | TAC | ACA | GCG | CCG | 1488 |
| Phe | Thr | Leu | Ala | Ala | Gly | Gly | Thr | Ala | Val | Trp | Gln | Tyr | Thr | Ala | Pro |      |
|     |     |     |     | 485 |     |     |     |     | 490 |     |     |     |     | 495 |     |      |
| GAA | ACG | TCG | CCG | GCG | ATC | GGC | AAT | GTG | GGT | CCC | ACC | ATG | GGC | CAG | CCG | 1536 |
| Glu | Thr | Ser | Pro | Ala | Ile | Gly | Asn | Val | Gly | Pro | Thr | Met | Gly | Gln | Pro |      |
|     |     |     | 500 |     |     |     |     | 505 |     |     |     |     | 510 |     |     |      |
| GGG | AAT | ATA | GTG | ACG | ATT | GAC | GGC | CGC | GGC | TTT | GGC | GGC | ACG | GCG | GGC | 1584 |
| Gly | Asn | Ile | Val | Thr | Ile | Asp | Gly | Arg | Gly | Phe | Gly | Gly | Thr | Ala | Gly |      |
|     |     | 515 |     |     |     |     | 520 |     |     |     |     | 525 |     |     |     |      |
| ACG | GTT | TAT | TTC | GGG | ACG | ACG | GCG | GTG | ACC | GGC | TCC | GGC | ATC | GTA | AGC | 1632 |
| Thr | Val | Tyr | Phe | Gly | Thr | Thr | Ala | Val | Thr | Gly | Ser | Gly | Ile | Val | Ser |      |
|     | 530 |     |     |     |     | 535 |     |     |     |     | 540 |     |     |     |     |      |
| TGG | GAG | GAC | ACG | CAG | ATT | AAG | GCG | GTC | ATA | CCG | AAG | GTC | GCG | GCG | GGC | 1680 |
| Trp | Glu | Asp | Thr | Gln | Ile | Lys | Ala | Val | Ile | Pro | Lys | Val | Ala | Ala | Gly |      |

| | | | | | | | | | | | | | | | | |
|---|---|---|---|---|---|---|---|---|---|---|---|---|---|---|---|---|
| 545 | | | | | 550 | | | | | 555 | | | | | 560 | |
| AAA | ACG | GGC | GTA | TCG | GTC | AAA | ACG | TCG | TCC | GGC | ACC | GCC | AGC | AAT | ACA | 1728 |
| Lys | Thr | Gly | Val | Ser | Val | Lys | Thr | Ser | Ser | Gly | Thr | Ala | Ser | Asn | Thr | |
| | | | | 565 | | | | 570 | | | | | 575 | | | |
| TTC | AAA | AGC | TTC | AAT | GTA | CTG | ACG | GGG | GAT | CAG | GTC | ACG | GTG | CGT | TTC | 1776 |
| Phe | Lys | Ser | Phe | Asn | Val | Leu | Thr | Gly | Asp | Gln | Val | Thr | Val | Arg | Phe | |
| | | | 580 | | | | 585 | | | | 590 | | | | | |
| CTG | GTC | AAT | CAA | GCC | AAT | ACC | AAT | TAC | GGA | ACA | AAT | GTT | TAT | CTT | GTC | 1824 |
| Leu | Val | Asn | Gln | Ala | Asn | Thr | Asn | Tyr | Gly | Thr | Asn | Val | Tyr | Leu | Val | |
| | | 595 | | | | 600 | | | | | 605 | | | | | |
| GGC | AAC | GCC | GCC | GAG | CTC | GGC | ACC | TGG | GAC | CCG | AAC | AAA | GCG | ATT | GGG | 1872 |
| Gly | Asn | Ala | Ala | Glu | Leu | Gly | Thr | Trp | Asp | Pro | Asn | Lys | Ala | Ile | Gly | |
| | 610 | | | | 615 | | | | | 620 | | | | | | |
| CCG | ATG | TAC | AAT | CAG | GTG | ATC | GCC | AAG | TAC | CCG | TCC | TGG | TAT | TAC | GAT | 1920 |
| Pro | Met | Tyr | Asn | Gln | Val | Ile | Ala | Lys | Tyr | Pro | Ser | Trp | Tyr | Tyr | Asp | |
| 625 | | | | 630 | | | | | 635 | | | | | 640 | | |
| GTC | AGC | GTG | CCG | GCG | GGG | ACA | AAG | CTG | GAT | TTT | AAA | TTT | ATT | AAA | AAG | 1968 |
| Val | Ser | Val | Pro | Ala | Gly | Thr | Lys | Leu | Asp | Phe | Lys | Phe | Ile | Lys | Lys | |
| | | | | 645 | | | | 650 | | | | | 655 | | | |
| GGC | GGC | GGT | ACG | GTG | ACT | TGG | GAA | GGC | GGG | GGC | AAC | CAT | ACG | TAC | ACG | 2016 |
| Gly | Gly | Gly | Thr | Val | Thr | Trp | Glu | Gly | Gly | Gly | Asn | His | Thr | Tyr | Thr | |
| | | | 660 | | | | 665 | | | | | 670 | | | | |
| ACG | CCG | GCC | AGC | GGC | GTA | GGG | ACG | GTG | ACG | GTG | GAC | TGG | CAA | AAT | | 2061 |
| Thr | Pro | Ala | Ser | Gly | Val | Gly | Thr | Val | Thr | Val | Asp | Trp | Gln | Asn | | |
| | | 675 | | | | 680 | | | | | 685 | | | | | |

( 2 ) INFORMATION FOR SEQ ID NO:10:

( i ) SEQUENCE CHARACTERISTICS:
        ( A ) LENGTH: 687 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Ser | Pro | Asp | Thr | Ser | Val | Asp | Asn | Lys | Val | Asn | Phe | Ser | Thr | Asp | Val |
| 1 | | | | 5 | | | | | 10 | | | | | 15 |
| Ile | Tyr | Gln | Ile | Val | Thr | Asp | Arg | Phe | Ala | Asp | Gly | Asp | Arg | Thr | Asn |
| | | | 20 | | | | | 25 | | | | | 30 | | |
| Asn | Pro | Ala | Gly | Asp | Ala | Phe | Ser | Gly | Asp | Arg | Ser | Asn | Leu | Lys | Leu |
| | | 35 | | | | | 40 | | | | | 45 | | | |
| Tyr | Phe | Gly | Gly | Asp | Trp | Gln | Gly | Ile | Ile | Asp | Lys | Ile | Asn | Asp | Gly |
| | 50 | | | | | 55 | | | | | 60 | | | | |
| Tyr | Leu | Thr | Gly | Met | Gly | Val | Thr | Ala | Leu | Trp | Ile | Ser | Gln | Pro | Val |
| 65 | | | | | 70 | | | | 75 | | | | | | 80 |
| Glu | Asn | Ile | Thr | Ser | Val | Ile | Lys | Tyr | Ser | Gly | Val | Asn | Asn | Thr | Ser |
| | | | | 85 | | | | | 90 | | | | | 95 | |
| Tyr | His | Gly | Trp | Trp | Ala | Arg | Asp | Phe | Lys | Gln | Thr | Asn | Asp | Ala | Phe |
| | | | 100 | | | | | 105 | | | | | 110 | | |
| Gly | Asp | Phe | Ala | Asp | Phe | Gln | Asn | Leu | Ile | Asp | Thr | Leu | Thr | Leu | Ile |
| | | | 115 | | | | | 120 | | | | | 125 | | |
| Thr | Ser | Arg | Ser | Asp | Arg | Leu | Arg | Pro | Gln | Pro | His | Val | Ser | Gly | Arg |
| | 130 | | | | | 135 | | | | | 140 | | | | |
| Ala | Gly | Thr | Asn | Pro | Gly | Phe | Ala | Glu | Asn | Gly | Ala | Leu | Tyr | Asp | Asn |
| 145 | | | | | 150 | | | | | 155 | | | | | 160 |
| Gly | Ser | Leu | Leu | Gly | Ala | Tyr | Ser | Asn | Asp | Thr | Ala | Gly | Leu | Phe | His |
| | | | | 165 | | | | | 170 | | | | | 175 | |
| His | Asn | Gly | Gly | Thr | Asp | Phe | Ser | Thr | Ile | Glu | Asp | Gly | Ile | Tyr | Lys |

|     |     |     |     |     | 180 |     |     |     |     | 185 |     |     |     |     | 190 |     |     |
| --- | --- | --- | --- | --- | --- | --- | --- | --- | --- | --- | --- | --- | --- | --- | --- | --- | --- |
| Asn | Leu | Tyr | Asp | Leu | Ala | Asp | Ile | Asn | His | Asn | Asn | Asn | Ala | Met | Asp |
|     |     | 195 |     |     |     |     | 200 |     |     |     |     | 205 |     |     |     |
| Ala | Tyr | Phe | Lys | Ser | Ala | Ile | Asp | Leu | Trp | Leu | Gly | Met | Gly | Val | Asp |
|     |     | 210 |     |     |     |     | 215 |     |     |     |     | 220 |     |     |     |
| Gly | Ile | Arg | Phe | Asp | Gly | Val | Lys | Gln | Tyr | Pro | Phe | Gly | Trp | Gln | Lys |
| 225 |     |     |     |     | 230 |     |     |     |     | 235 |     |     |     |     | 240 |
| Ser | Phe | Val | Ser | Ser | Ile | Tyr | Gly | Gly | Asp | His | Pro | Val | Phe | Thr | Phe |
|     |     |     |     | 245 |     |     |     |     | 250 |     |     |     |     | 255 |     |
| Gly | Glu | Trp | Tyr | Leu | Gly | Ala | Asp | Gln | Thr | Asp | Gly | Asp | Asn | Ile | Lys |
|     |     |     | 260 |     |     |     |     | 265 |     |     |     |     | 270 |     |     |
| Phe | Ala | Asn | Glu | Ser | Gly | Met | Asn | Leu | Leu | Asp | Phe | Glu | Tyr | Ala | Gln |
|     |     | 275 |     |     |     |     | 280 |     |     |     |     | 285 |     |     |     |
| Glu | Val | Arg | Glu | Val | Phe | Arg | Asp | Lys | Thr | Glu | Thr | Met | Lys | Asp | Leu |
|     | 290 |     |     |     |     | 295 |     |     |     |     | 300 |     |     |     |     |
| Tyr | Glu | Val | Leu | Ala | Ser | Thr | Glu | Ser | Gln | Tyr | Asp | Tyr | Ile | Asn | Asn |
| 305 |     |     |     |     | 310 |     |     |     |     | 315 |     |     |     |     | 320 |
| Met | Val | Thr | Phe | Ile | Asp | Asn | His | Asp | Met | Asp | Arg | Phe | Gln | Val | Ala |
|     |     |     |     | 325 |     |     |     |     | 330 |     |     |     |     | 335 |     |
| Gly | Ser | Gly | Thr | Arg | Ala | Thr | Glu | Gln | Ala | Leu | Ala | Leu | Thr | Leu | Thr |
|     |     |     | 340 |     |     |     |     | 345 |     |     |     |     | 350 |     |     |
| Ser | Arg | Gly | Val | Pro | Ala | Ile | Tyr | Tyr | Gly | Thr | Glu | Gln | Tyr | Met | Thr |
|     |     | 355 |     |     |     |     | 360 |     |     |     |     | 365 |     |     |     |
| Gly | Asp | Gly | Asp | Pro | Asn | Asn | Arg | Ala | Met | Met | Thr | Ser | Phe | Asn | Thr |
|     | 370 |     |     |     |     | 375 |     |     |     |     | 380 |     |     |     |     |
| Gly | Thr | Thr | Ala | Tyr | Lys | Val | Ile | Gln | Ala | Leu | Ala | Pro | Leu | Arg | Lys |
| 385 |     |     |     |     | 390 |     |     |     |     | 395 |     |     |     |     | 400 |
| Ser | Asn | Pro | Ala | Ile | Ala | Tyr | Gly | Thr | Thr | Thr | Glu | Arg | Trp | Val | Asn |
|     |     |     |     | 405 |     |     |     |     | 410 |     |     |     |     | 415 |     |
| Asn | Asp | Val | Leu | Ile | Ile | Glu | Arg | Lys | Phe | Gly | Ser | Ser | Ala | Ala | Leu |
|     |     |     | 420 |     |     |     |     | 425 |     |     |     |     | 430 |     |     |
| Val | Ala | Ile | Asn | Arg | Asn | Ser | Ser | Ala | Ala | Tyr | Pro | Ile | Ser | Gly | Leu |
|     |     | 435 |     |     |     |     | 440 |     |     |     |     | 445 |     |     |     |
| Leu | Ser | Ser | Leu | Pro | Ala | Gly | Thr | Tyr | Ser | Asp | Val | Leu | Asn | Gly | Leu |
| 450 |     |     |     |     | 455 |     |     |     |     | 460 |     |     |     |     |     |
| Leu | Asn | Gly | Asn | Ser | Ile | Thr | Val | Gly | Ser | Gly | Gly | Ala | Val | Thr | Asn |
| 465 |     |     |     |     | 470 |     |     |     |     | 475 |     |     |     |     | 480 |
| Phe | Thr | Leu | Ala | Ala | Gly | Gly | Thr | Ala | Val | Trp | Gln | Tyr | Thr | Ala | Pro |
|     |     |     |     | 485 |     |     |     |     | 490 |     |     |     |     | 495 |     |
| Glu | Thr | Ser | Pro | Ala | Ile | Gly | Asn | Val | Gly | Pro | Thr | Met | Gly | Gln | Pro |
|     |     |     | 500 |     |     |     |     | 505 |     |     |     |     | 510 |     |     |
| Gly | Asn | Ile | Val | Thr | Ile | Asp | Gly | Arg | Gly | Phe | Gly | Gly | Thr | Ala | Gly |
|     |     | 515 |     |     |     |     | 520 |     |     |     |     | 525 |     |     |     |
| Thr | Val | Tyr | Phe | Gly | Thr | Thr | Ala | Val | Thr | Gly | Ser | Gly | Ile | Val | Ser |
|     | 530 |     |     |     |     | 535 |     |     |     |     | 540 |     |     |     |     |
| Trp | Glu | Asp | Thr | Gln | Ile | Lys | Ala | Val | Ile | Pro | Lys | Val | Ala | Ala | Gly |
| 545 |     |     |     |     | 550 |     |     |     |     | 555 |     |     |     |     | 560 |
| Lys | Thr | Gly | Val | Ser | Val | Lys | Thr | Ser | Ser | Gly | Thr | Ala | Ser | Asn | Thr |
|     |     |     |     | 565 |     |     |     |     | 570 |     |     |     |     | 575 |     |
| Phe | Lys | Ser | Phe | Asn | Val | Leu | Thr | Gly | Asp | Gln | Val | Thr | Val | Arg | Phe |
|     |     |     | 580 |     |     |     |     | 585 |     |     |     |     | 590 |     |     |
| Leu | Val | Asn | Gln | Ala | Asn | Thr | Asn | Tyr | Gly | Thr | Asn | Val | Tyr | Leu | Val |
|     |     | 595 |     |     |     |     | 600 |     |     |     |     | 605 |     |     |     |

| | | | | | | | | | | | | | |
|---|---|---|---|---|---|---|---|---|---|---|---|---|---|
|Gly|Asn|Ala|Ala|Glu|Leu|Gly|Thr|Trp|Asp|Pro|Asn|Lys|Ala|Ile|Gly
| |610| | | |615| | | | |620| | | |

Gly Asn Ala Ala Glu Leu Gly Thr Trp Asp Pro Asn Lys Ala Ile Gly
    610             615                 620

Pro Met Tyr Asn Gln Val Ile Ala Lys Tyr Pro Ser Trp Tyr Tyr Asp
625             630                 635                     640

Val Ser Val Pro Ala Gly Thr Lys Leu Asp Phe Lys Phe Ile Lys Lys
                645                 650                 655

Gly Gly Gly Thr Val Thr Trp Glu Gly Gly Asn His Thr Tyr Thr
            660             665             670

Thr Pro Ala Ser Gly Val Gly Thr Val Thr Val Asp Trp Gln Asn
            675             680             685

(2) INFORMATION FOR SEQ ID NO:11:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:11:

Asn Thr Ala Tyr Gly Tyr Ala Tyr His Gly Tyr Trp Met Lys
   1               5                   10

(2) INFORMATION FOR SEQ ID NO:12:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:12:

Ser Gly Val Asn Asn Thr Ala Tyr His Gly Tyr Trp Pro Arg
   1               5                   10

(2) INFORMATION FOR SEQ ID NO:13:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: N-terminal (xi) SEQUENCE DESCRIPTION: SEQ ID NO:13:

Glu Asn Phe Gly Thr Ala Asp Asp
   1               5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:14:

```
Ala  Ala  Phe  Gly  Ser  Phe  Thr  Asp
1                   5
```

( 2 ) INFORMATION FOR SEQ ID NO:15:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:15:

```
Asp  Met  Leu  Leu  Met  Val  Asp  Ile  Val  Thr  Asn  His  Tyr  Gly  Ser
1                   5                        10                       15
```

( 2 ) INFORMATION FOR SEQ ID NO:16:

( i ) SEQUENCE CHARACTERISTICS:
        ( A ) LENGTH: 15 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:16:

```
Asn  Ile  Lys  Val  Val  Met  Asp  Phe  Ala  Pro  Asn  His  Thr  Asn  Pro
1                   5                        10                       15
```

( 2 ) INFORMATION FOR SEQ ID NO:17:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA"

( i i i ) HYPOTHETICAL: NO ( i v ) ANTI-SENSE: NO ( x i ) SEQUENCE DESCRIPTION: SEQ ID NO:17:

TATCATGGTT ACTGGATGAA G  21

( 2 ) INFORMATION FOR SEQ ID NO:18:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: other nucleic acid
        ( A ) DESCRIPTION: /desc ="Synthetic DNA"

( i i i ) HYPOTHETICAL: NO ( i v ) ANTI-SENSE: NO ( x i ) SEQUENCE DESCRIPTION: SEQ ID NO:18:

TATCACGGTT ACTGGGCGAG G  21

VARIANT-TYPE CARBOHYDRATE HYDROLASE, VARIANT GENE OF THE ENZYME AND METHOD FOR PRODUCING OLIGOSACCHARIDE USING THE ENZYME

FIELD OF THE INVENTION

The present invention relates to a variant-type carbohydrate hydrolase that has been increased in transglycosylation activity. In particular this invention relates to an amylase or another carbohydrate hydrolase analogous to amylase, wherein the tyrosine residue is substituted with another amino acid residue, which tyrosine residue constitutes the active center of the enzyme. Furthermore, the present invention relates to a gene or a DNA sequence with a mutation introduced into the base sequence that encodes the tyrosine residue of the carbohydrate hydrolase; it relates to a variant enzyme in which the tyrosine residue of the carbohydrate hydrolase is substituted; it relates to a vector or a transformant which comprises the DNA sequence; and it relates to a method for producing a variety of oligosaccharides and the like by using the variant enzyme.

BACKGROUND OF THE INVENTION

In recent years, as artificial sweeteners that can replace sugar without causing tooth decay and as materials for functional foods, a variety of oligosaccharides of various polymerization degrees have drawn attention and have been put to practical use.

The present inventors have already reported that transglycosylation activity is elevated in a variant-type α-amylase (SfamyW84L), in which a leucine residue is substituted for the tryptophan residue at position 84 of the amino acid sequence of the α-amylase (Sfamy) which is obtained from the yeast *Saccharomycopsis fibuligera*; and that a method for producing a malto-oligosaccharide of a polymerization degree of 7 or more, using the said variant-type α-amylase (unexamined Japanese Patent Publication No. 108386/1992). However, it has not yet been made clear the mechanism by which the transglycosylation activity of the enzyme Sfamy W84L is elevated. Thus, no method has yet been found for elevating the transglycosylation activity of Sfamy and other carbohydrate hydrolases in a rational manner.

BRIEF SUMMARY OF THE INVENTION

The present inventors have made intensive investigations aimed at rationally increasing the transglycosylation activity of carbohydrate hydrolases. As a result, the inventors have found that the tyrosine residue corresponding to the Y83 residue of the Sfamy is completely preserved original spatial arrangement at a homologous position in numerous carbohydrate hydrolases analogous to amylase, such as α-amylase and cyclomaltodextrin glucanotransferase. Further, the inventors have found that these tyrosine residues are present in the active centers of the enzymes, and that the phenolic OH group of the tyrosine residues may be considered to have a definitely important function to provide $H_2O$ molecules to a reaction intermediate during each enzyme's enzymatic reaction. Therefore, the inventors have found that by substituting another amino acid residue for the tyrosine residue, thereby deteriorating the function of the tyrosine residue during hydrolysis, the transglycosylation activity of the carbohydrate hydrolases can be increased.

The present invention has been achieved based on the above findings.

Therefore, an object of the present invention is to provide a variant-type carbohydrate hydrolase that has been increased in transglycosylation activity, in particular to provide a hydrolase substituted another amino acid residue for the tyrosine residue that is present in the active center of the hydrolase, which hydrolase is an amylase or another carbohydrate hydrolase analogous to amylase.

Another object of the present invention is to provide a gene with mutation introduced into the base sequence that encodes the tyrosine residue of the carbohydrate hydrolase.

Further, another object of the present invention is to provide a method for producing a variety of oligosaccharides and the like by using the variant-type carbohydrate hydrolase that has been increased in transglycosylation activity.

Still another object of the present invention is to provide a method for rationally increasing the transglycosylation activity of enzyme that is an amylase or an enzyme analogous to amylase.

Other and further objects, features, and advantages of the invention will appear more evident from the following description, taken in connection with the accompanying drawings.

BRIEF DESCRIPTION OF THE DRAWING

FIG. 1 is a drawing that comparatively shows the amino acid sequences (SEQ ID NOS:11–16) in three preserved-regions immediately next to the amino terminus of wild-type Sfamy and wild-type cyclomaltodextrin glucanotransferase (CGTase).

DETAILED DESCRIPTION OF THE INVENTION

The present invention is to provide:

1. A variant-type carbohydrate hydrolase, selected from a group consisting of α-amylase and cyclomaltodextrin glucanotransferase, wherein the hydrolase's tyrosine residue, which is present in the active center of the enzyme, and which functions to provide $H_2O$ molecules to a reaction intermediate, is substituted (replaced) with another amino acid residue;

2. The variant-type carbohydrate hydrolase according to the above item 1, wherein the tyrosine residue is present within a 5 angstroms range from three acidic amino acid residues which are immediate catalytic residues, and wherein the tyrosine residue has a function to provide $H_2O$ molecules to a reaction intermediate;

3. A variant α-amylase, wherein the tyrosine residue at position 83 of the amino acid sequence of the α-amylase from *Saccharomycopsis fibuligera* is substituted with a phenylalanine, SEQ ID NO.:2, a tryptophan, SEQ ID NO.:4, a leucine, SEQ ID NO.:6, or an asparagine residue, SEQ ID NO.:8;

4. A variant α-amylase gene, wherein the base sequence at positions 247 to 249 of said gene (positions 325 to 327 of the structural gene) in the α-amylase gene from *Saccharomycopsis fibuligera* is mutated into one of TTC, SEQ ID NO.:1 TGG, SEQ ID NO.:5, CTC, SEQ ID NO.:3 or AAC, SEQ ID NO.:7;

5. A method for producing a malto-oligosaccharide of a polymerization degree of 7 or more, comprising subjecting a substrate malto-oligosaccharide to transglycosylation reaction with the variant α-amylase according to the above variant in item 3;

6. A variant cyclomaltodextrin glucanotransferase, SEQ ID NO.:10, wherein the tyrosine residue at position 100 of the amino acid sequence of the cyclomaltodextrin glucanotransferase from *Bacillus macerans* is substituted with a tryptophan residue;

7. A variant cyclomaltodextrin glucanotransferase gene, SEQ ID NO.:9, wherein the base sequence at positions 299 to 300 of said gene (positions 380 to 381 of the structural gene) of the cyclomaltodextrin glucanotransferase from *Bacillus macerans* is mutated into GG; and 8. A method for producing oligosaccharides containing higher concentrations of α-maltopyranosyl-β-D-fructofuranoside and α-maltotripyranosyl-β-D-fructofuranoside, comprising subjecting substrates of starch and sucrose to transglycosylation reaction with the variant cyclomaltodextrin glucanotransferase according to the above variant in item 6.

The present invention will now be explained in details hereinbelow.

The present inventors have found that substitution of the tryptophan residue at position 84 of the variant-type SfamyW84L which already reported, might have an influence on the adjacent tyrosine residue (Y83) at position 83, resulting in a modification of the Y83 residue's function, to thereby increase the transglycosylation activity. In other words, it has been found that the principal factor for increasing the transglycosylation activity is based on eliminating the function of the Y83 residue.

Conventionally, it has been known as a general empirical rule that not only the species but also the relative spatial geometry of an amino acid residue, which residue is most important for expression of the activity of an enzyme, is kept as it is in analogous enzymes, despite that they come from different organisms.

Examination was conducted to identify where the tyrosine residue corresponding to the Y83 residue of Sfamy was positioned on the steric structure in the α-amylases enzymes such as Sfamy, derived from 10 species of organisms. As a result, it was found that the configuration of the tyrosine residue is completely preserved in all of the 10 types of α-amylases.

Ten types of α-amylases from the following organisms were examined:

1. Actinomyces (*Streptomyces hyqroscopicus*);
2. Pig pancreas;
3. *Bacillus subtilis;*
4. *B. ciculans;*
5. *Saccharomycopsis fibuligera;*
6. *Aspergillus oryzae;*
7. *B. stearothermophilus;*
8. *B. lichenformis;*
9. *B. amyloliguefaciens*; and
10. barley.

Based on the data concurrently demonstrating the primary sequences of the 10 types of α-amylases from the different organisms, comparative examination was done on the steric structure of the enzyme Sfamy, to determine how the amino acid residues constituting the active site of the enzyme were conserved. Consequently, it was found that one Tyr residue corresponding to the Y83 of Sfamy was present near the three, direct catalytic residues (two Asp residues and one Glu residue), i.e. within a 5 angstroms range from these residues, and that these four residues were completely preserved original spatial arrangement in the 10 types of α-amylase proteins described above, to form each enzymatic active center. Thereby, the tyrosine residue corresponding to the Y83 residue of Sfamy may possibly have an important function through its phenolic OH to provide $H_2O$ molecules to the intermediate of a enzymatic reaction.

Then, attention was focused on the Tyr residue (Y) forming the enzymatic active center in the α-amylases. Examination was conducted to determine if the Y residue might be present in the following cyclomaltodextrin glucanotransferase, which is analogous to α-amylase. Using Sfamy as an α-amylase, comparison was made of the amino acid sequences of the two enzymes, i.e. Sfamy and the below-mentioned CGTase.

CGTase: cyclomaltodextrin glucanotransferase, derived from *Bacillus macerans.*

From the results of the comparison of the primary amino acid sequences of the two enzymes, six highly preserved homologous regions were identified. Among the six regions highly preserved spatial arrangement, three preserved regions immediately next to the amino terminus (N-terminus) have their amino acid sequences shown in FIG. 1.

The Y residue in focus, corresponding to the Y83 residue of the enzyme Sfamy, is present in region 1, and the residue is also preserved at the homologous position in cyclomaltodextrin glucanotransferase, as shown in the confined part in region 1 of FIG. 1, SEQ ID NO.:11 and SEQ ID NO.:12. It was found that in cyclomaltodextrin glucanotransferase, the Tyr residue was also present in the proximity of three directly catalytic residues, i.e. two Asp residues and one Glu residue, namely within 5 angstroms from these residues, as in Sfamy as described above. Thereby, the tyrosine residue corresponding to the Y83 residue of Sfamy was present at position 100 in CGTase.

Furthermore, FIG. 1 shows clearly that these three highly preserved regions were arranged at nearly equal intervals.

Based on the findings described above and the fact that the amino acid residues (Tyr residue, Glu residue, and two Asp residues) being present in these three regions form an active center of the enzyme in α-amylase, it is considered that the completely preserved Y residue that is present in region 1 and that corresponds to the Y83 residue of Sfamy, may be present in the active center of the enzyme in cyclomaltodextrin glucanotransferase, to perform a definitely important function in the hydrolysis of substrates. Also, it is suggested that the tyrosine residue functions through its phenolic OH group to provide $H_2O$ molecules to a reaction intermediate during enzymatic reaction.

These findings suggest that the transglycosylation activity of the two types of enzymes analogous to amylase, i.e. Sfamy and CGTase, can be increased by substituting the tyrosine residue that constitutes the active center of each enzyme with another amino acid residue.

In the present invention, the "another amino acid residue" is introduced to lower the hydrolysis activity of the carbohydrate hydrolase. The another amino acid residue is an amino acid residue which has no phenolic OH group. Every amino acid other than tyrosine among 20 types of natural amino acid has no phenolic OH group, and can be used as the another amino acid residue.

A method for preparing a variant enzyme of the present invention, and the effects on the enzyme activity of the substitution of the tyrosine residue present in the active center of the variant enzyme are described first.

In order to elucidate the function of the Y residue that is present in the region 1 of FIG. 1, which Y residue is also present in the above-mentioned two types of enzymes that are analogous to amylase, variant enzymes of the two enzymes (Sfamy and CGTase) were prepared, wherein the Y83 residue of Sfamy and the Y100 residue of CGTase were substituted with another amino acid residue, respectively. Then, examination was conducted to elucidate the effects of this substitution on the carbohydrate hydrolysis activity and the transglycosylation activity of these enzymes.

1. Variant-type Sfamy

As one example of α-amylase, variant-type enzymes were prepared, wherein the Y83 residue of Sfamy was substituted with one of F, W, L, or N residue, to assess the transglycosylation activity.

The Kunkel method was employed for preparing variant genes.

From a plasmid pSfα1 that carried the gene of the enzyme Sfamy, an EcoRI-PstI fragment (2.5 kb) containing the Sfamy structural gene was subcloned into the multi-cloning site of M13 phage. An M13 phage replicated form (RF) DNA containing the objective DNA fragment was infected into a uracil-DNA glycosylase (ung) defective-$E.$ $coli$ strain CJ236, to recover the phage particles from the culture supernatant of the $E.$ $coli$ strain. From the recovered phage particles, uracil single-stranded DNA (minus (−) chain) was obtained. By annealing the single-stranded DNA with each of the synthetic oligonucleotides containing mutation in the coding region that encoded the Y residue, and thereafter by reacting $T_4$ DNA polymerase with the annealed product, to repair the single strand (plus (+) chain), each double-stranded DNA (U-RF DNA) was prepared. After introducing each of the DNAs into $ung^+$ $E.$ $coli.$, the phage particle was recovered from the $E.$ $coli$ culture supernatant, to prepare each single-stranded DNA. By analyzing the base sequence of the single-stranded DNAs, RF DNAs with the objective mutation were selected.

A 2.5 kb EcoRI-PstI fragment cleaved out from each of the RF DNAs was inserted into and ligated with the multi-cloning site of a yeast expression vector YEp351, to prepare each of expression vectors of the variant enzymes, i.e. pSA5Y83F, pSA5Y83W, pSA5Y83L, and pSA5Y83N.

Through the transformation of each of these expression vectors in strain KK4 of the baker's yeast $Saccharomyces$ $cerevisiae$, transformants KK4:pSA5Y83F, KK4:pSA5Y83W, KK4:pSA5Y83L, and KK4:pSA5Y83N were obtained. Similarly, a transformant KK4:pSA5 carrying the gene of the wild-type enzyme was also prepared. After culturing these transformants in the YPD medium, various purification procedures were employed to supernatant of the culture, to prepare purified variant enzymes, i.e. SfamyY83F, SfamyY83W, SfamyY83L, and SfamyY83N, as well as the purified wild-type enzyme, Sfamy.

The four variant enzymes: SfamyY83F, SfamyY83W, SfamyY83L, and SfamyY83N, prepared in accordance with the present invention, all exhibited far stronger transglycosylation activity than carbohydrate hydrolysis activity, to individually prepare various characteristic products depending on the polymerization degree of each starting substrate.

When maltoheptaose ($G_7$) was a substrate, for example, it was partially decomposed into lower molecules, but was mostly transformed into $G_{10}$, $G_{11}$ and $G_{12}$. When maltopentaose ($G_5$) was a substrate, transglycosylation products, $G_7$ and $G_8$, were produced; from maltohexaose, ($G_6$), $G_9$ was produced.

Through separation and purification procedures, such as gel filtration, malto-oligosaccharides of longer chains by specific chain lengths than those of these substrates were produced from the resulting reaction mixtures.

The optimum conditions for the above transglycosylation enzyme reactions are approximately a temperature of 30° C. and pH 5.5, for example. The reaction time varies depending on the polymerization degree and concentration of a substrate and the enzyme concentration, but the general satisfactory reaction time is 15 minutes.

The physicochemical properties of the variant-type α-amylases will now be described hereinbelow.

(1) Function

The variant enzymes of the present invention exhibit far stronger transglycosylation activity than the wild-type enzyme, so the variant enzymes exhibit strong transglycosylation activity at a lower substrate level (2 mM), at which level the wild-type enzyme does not exhibit transglycosylation activity. When the variant enzymes react with malto-oligosaccharide, malto-oligosaccharides of a longer chain than that of the initial substrate are prepared. Various characteristic products are prepared, depending on the polymerization degree of each starting substrate. When maltoheptaose ($G_7$) is a substrate, for example, it is partially decomposed into lower molecules, but is mostly transformed into $G_{10}$, $G_{11}$, and $G_{12}$. When maltopentaose ($G_5$) is a substrate, $G_7$ and $G_8$ are prepared; from maltohexaose ($G_6$) as a substrate, $G_9$ is prepared.

(2) Substrate specificity

The variant enzymes of the present invention react well with starch, glycogen, and malto-oligosaccharide, but they do not react with pullulan, dextran, or cellulose.

(3) Optimum pH and stable pH range

The optimum pH for the variant enzymes is from pH 5.4 to 5.6 at 40° C., and the stable pH range is from pH 4 to 10.

(4) Optimum temperature

The optimum temperature for the variant enzymes is at 50° C. at pH 5.5.

(5) Inactivating conditions

Under heating at 70° C. and pH 5.5 for 10 minutes, the remaining activity of each of the variant enzymes is at a ratio of 10%. The enzymes are unstable at pH 4 or less, or at pH 10 or more.

(6) Inhibition, activation, and stabilization

The variant enzymes are inhibited in the presence of mercury, lead, and EDTA. The enzymes are stabilized by calcium ion.

(7) Assay of transglycosylation activity

Terminating the enzyme reaction after the prescribed period of time, the reaction products were spread out and separated by paper chromatography; then the products were sensitized with glucoamylase treatment, followed by development with silver nitrate. Furthermore, the molecular species of individual spots were identified and analyzed quantitatively with a densitometer; the change of the products through the enzyme reaction was analyzed over time, to determine transglycosylation activity.

(8) Molecular weight of the enzymes

The molecular weight of each of the variant enzymes is 51,000 (by disk gel electrophoresis).

2. Variant-type CGTase

A variant enzyme (CGTaseY100W) was prepared, wherein the Y100 residue (corresponding to Y83 residue of Sfamy) of cyclomaltodextrin glucanotransferase (CGTase) derived from $Bacillus$ $macerans$, which is an enzyme analogous to α-amylase, was substituted with a W residue. The transglycosylation activity of CGTaseY100W was determined.

First, CGTase gene was cloned.

The chromosomal DNA from $B.$ $macerans$ IAM 1243 strain was treated with Sau3AI and Hind III; then it was ligated with pBR322; then it was then inserted into $E.$ $coli$ HB101.

The cloning strain carrying CGTase gene was detected by iodine starch reaction on an agar medium containing starch. Consequently, a recombinant plasmid pMAC1 with a 4 kb DNA containing CGTase gene inserted was prepared. The pMAC1 was partially digested with Sau3AI; then it was inserted and ligated in the BamHI site of a plasmid pHY300PLK, to prepare pMAA1. The plasmid was introduced in an α-amylase-defective B. subtilis strain 207-25, to prepare a transformant strain 207-25:pMAA1; then it was tetracycline-resistant and had halo formation potency during iodine starch reaction on starch-agar medium. Purified CGTases obtained from the culture supernatants of B. macerans IAM 1243 strain and B. subtilis 207-25:pMAA1 were subjected to enzyme-reaction with soluble starch, and the resulting enzyme-reaction products were analyzed by paper chromatography. The main reaction products of the two enzyme reactions were α-cyclodextrin, and the two reactions could not be discriminated from each other in terms of their enzymatic natures. Furthermore, the base sequence of the DNA fragment inserted into the plasmid pMAA1 was determined. The base sequence of the structural gene of CGTase, which base sequence consisted of 2142 bp, was determined, and translated into the amino acid sequence of CGTase.

Variant gene was prepared by the Kunkel method.

First, an XbaI-EcoRI fragment (2.5 kb) containing the CGTase structural gene was subcloned from pMAA1 into M13 phase, and the M13 phage RF DNA containing the objective DNA fragment was infected into a ung$^-$ E. coli strain CJ236. The phage particle was then recovered from the culture supernatant of the E. coli strain, to prepare uracil single-stranded DNA (minus (−) chain). By annealing the single-stranded DNA and a synthetic oligonucleotide having a mutation in the coding region encoding the Y100 residue, and then repairing the single strand (plus (+) chain), a double-stranded DNA (U-RF DNA) was prepared. After inserting the DNA into ung$^+$ E. coli, the phage particle was recovered from the E. coli culture supernatant, to prepare RF DNA.

After analyzing the base sequence of the RF DNA, a DNA fragment (XbaI-EcoRI fragment of 2.5 kb) carrying the objective mutation was incised out; then it was inserted and ligated in the XbaI-EcoRI site of the B. subtilis expression vector, PHY300PLK, whereby a variant enzyme expression vector pMAA1Y100W was prepared.

Through the transformation of these expression vectors, which individually carried the wild-type enzyme gene and the variant-type enzyme gene, into the B. subtilis 207-25 strain, transformants B. subtilis 207-25:pMAA1 and 207-25:pMAA1 Y100W were obtained.

After culturing these transformants in the NB medium supplemented with 1% soluble starch, various purification procedures were employed to recover the purified wild-type enzyme and the purified variant-type enzyme, i.e. CGTase Y100W, from the culture supernatants.

Besides cyclodextrin production via CGTase action with starch, CGTase transfers malto-oligosaccharide into sugar receptors if the receptor molecules are present along with starch. The variant enzyme, CGTaseY100W, prepared in accordance with the present invention, exhibited far stronger transglycosylation activity than the wild-type enzyme.

When CGTase Y100W reacts with a solution containing 5% soluble starch and 5% sucrose, for example, the production of a small amount of cyclodextrin is observed at the initial stage, but the prepared cyclodextrin is decomposed again and is eliminated at the later stage. In this reaction, 50% of the existing sucrose is utilized as the receptor for the action of transglycosylation. In the oligosaccharides prepared, $G_2F$ (α-maltopyranosyl-β-D-fructofuranoside) and $G_3F$ (α-maltotripyranosyl-β-D-fructofuranoside) are contained at ratios of 21% and 12%, respectively, in addition to sucrose at a ratio of 24%. Thus, the use of the variant enzyme CGTase Y100W enables highly efficient production of an oligosaccharide containing $G_2F$ and $G_3F$.

The optimum conditions for reacting the transglycosylase enzyme are approximately 50° C. and pH 5.5, for example. The reaction time varies depending on the concentration of a substrate and the enzyme concentration. Generally, a satisfactory reaction time is 15 minutes.

The physico-chemical properties of the variant-type CGTase will now be described hereinbelow.

(1) Function

The variant enzyme of the present invention exhibits far stronger transglycosylation activity than the wild-type enzyme. When the variant enzyme reacts with soluble starch in the presence of sucrose as the receptor, a glucosyl group, a maltosyl group, and a maltotriosyl group are transferred into the receptor (sucrose), to prepare malto-oligosaccharide derivatives, which are of various chain lengths and which contain fructose at the reducing end thermini; this derivative production is more efficient than the same reaction involving the wild-type enzyme.

(2) Substrate specificity

The variant enzyme reacts well with starch and malto-oligosaccharide, but it does not react with pullulan, dextran, or cellulose.

(3) Optimum pH and stable pH range

The optimum pH of the variant enzyme is from pH 5.4 to 5.6 at 40° C., and the stable pH range is from pH 3 to 11.

(4) Optimum temperature

The optimum temperature of the variant enzyme is 60° C. at pH 5.5.

(5) Inactivating conditions

Under heating at 70° C. and pH 5.5 for 10 minutes, the remaining activity of the variant enzyme is at a ratio of 30%. The enzyme is unstable at pH 3 or less, or at pH 11 or more.

(6) Inhibition, activation, and stabilization

The variant enzyme is inhibited in the presence of mercury, lead, and EDTA. The enzyme is stabilized by using calcium ion.

(7) Assay of transglycosylation activity

Terminating the enzyme reaction after the prescribed period of time, the reaction products were spread out and separated by paper chromatography; then the products were sensitized with glucoamylase treatment, followed by development with silver nitrate. Furthermore, the molecular species of individual spots were identified and analyzed quantitatively with a densitometer; the change of the products through the enzyme reaction was analyzed over time, to determine transglycosylation activity.

(8) Molecular weight of the enzyme

The molecular weight of the variant enzyme is 74,000 (by disk gel electrophoresis).

Each of the variant-type carbohydrate hydrolases in accordance with the present invention exhibits far greater carbohydrate hydrolysis activity than the wild type, due to the mutation of the tyrosine residue present in the active center of the enzyme. The use of each of the variant-type enzymes of the present invention enables the production of a specific malto-oligosaccharide of a high polymerization degree of 7 or more, or the production of an oligosaccharide containing high concentrations of $G_2F$ and $G_3F$, both at a high yield. Hence, the variant enzymes can preferably be used for large-scale industrial production of a variety of oligosaccharides.

The variant genes of the present invention enable the preparation of variant enzymes, belonging to the group of amylase or its analogous carbohydrate hydrolase, that are rationally provided with transglycosylation activity essential for the production of useful enzymatic products, such as malto-oligosaccharide.

Next the present invention will be described in detail in accordance with examples, but the invention is not limited to these examples.

EXAMPLE 1

A method for preparing variant-type Sfamys Variant genes were prepared, wherein the structural gene of Sfamy was mutated by site-directed mutagenesis.

The variant genes were prepared according to the Kunkel procedure.

From a plasmid pSfα1 carrying the Sfamy gene, a 2.5 kb EcoRI-PstI DNA fragment carrying the Sfamy structural gene was inserted in and linked with the multi-cloning site of M13 phage mp18. The M13 phage replicated form (RF) DNA containing the objective DNA fragment was infected in a uracil-DNA glycosylase (ung)-defective $E.$ $coli$ strain CJ236. The infected bacterium was cultured in the LB medium (1% Bactotripton, 0.5% yeast extract, 0.5% NaCl, and 0.1% glucose). From the culture supernatant, the phage particle was recovered and extracted with phenol, to yield uracil-containing single-stranded DNA (minus (−) chain).

In order to substitute the Y83 residue (codon; TAC) with respectively each of phenylalanine (codon; TTC), tryptophan (codon; TGG), leucine (codon; CTC), and asparagine (codon; AAC), four types of 21-mer oligonucleotides were synthesized, in which the underlined codon in the oligonucleotide sequence 5' TAT CAT GGT TAC TGG ATG AAG 3', SEQ ID NO.:17, was substituted with each of the codons for the above-mentioned objective four amino acids. By annealing the single-stranded DNA containing uracil with each of the synthetic oligonucleotides, followed by effecting the action of $T_4$ DNA polymerase and $T_4$ DNA ligase, each single strand (plus (+) chain) was repaired, to prepare each double-stranded DNA (U-RF DNA). By inserting each of the U-RF DNAs into ung$^+$ $E.$ $coli$ strain (MV1190 strain), each DNA strand containing uracil was decomposed with the ung to recover the phage particle in replication or RF DNA from the DNA strand that had a mutation introduced. Specifically, each U-RF DNA was introduced into MV1190 strain with DNA receptivity enhanced by the calcium chloride method; the U-RF DNA was then inoculated on the LB solid medium together with the indicator bacterium (MV1190 strain), followed by overnight incubation at 37° C. The phage particle from the plaques that had grown by the next day was transferred into the TE solution (10 mM Tris-HCl buffer, pH 8.0, containing 1 mM EDTA) and was kept at 4° C. Simultaneously, four clones among them were separately infected in the MV1190 strain in 2 ml of LB liquid medium, followed by culturing for 7 hours at 37° C. The culture medium was centrifuged, and from the resulting supernatant, the phage particle was recovered as the precipitate in polyethylene glycol; the particle was then treated with phenol, to isolate each single-stranded DNA. The base sequences of the single-stranded DNAs were then determined, to selectively isolate phage clones that had an accurately inserted mutation.

The base sequences of the variant genes were determined by the dideoxy method. Ten types of 17-mer oligonucleotides ($P_1$ to $P_{10}$) were synthesized, which have complementarity with the minus chain of the structural gene, and which cover the entire structural gene. Among them, an oligonucleotide $P_2$ (2.5 ng), which was located at the 5' terminus of the mutated site (position 325 to position 327 of the base sequence of the structural gene i.e., positions 247 to 249 in SEQ ID NOS:1,3,5, and 7), and which corresponded to position 267 to position 283, i.e., positions 189 to 205 in SEQ ID NOS.:1,3,5, and 7, was annealed with 1 μg of each of the previously isolated single-stranded DNAs (minus (−) chains) under heating, with subsequent annealing. Using 5 μCi of [α-$^{32}$P]dCTP and a commercially available sequencing kit, elongation, labeling, and termination reactions of the plus chains of the resulting annealed products were carried out at 37° C.

Each of the samples was heated at 100° C. for 2 minutes, followed by rapid cooling in ice; then it was added to 8% acrylamide gel (thickness; 0.2 mm, length; 50 cm) containing 8.3M urea, followed by electrophoresis in the TBE solution (45 mM Tris-borate buffer, pH 8.3 containing 1 mM EDTA) for 2 hours. After electrophoresis, each of the gels was transferred and dried on a filter. Then, each of the filters was used to expose an X-ray film at −80° C. for 3 hours, to obtain an autoradiogram. By identifying the bands developed thereon sequentially, the base sequences were determined. Through the above procedure, phage clones were prepared, wherein a part of the base sequence, corresponding to the tyrosine (Y) codon at position 325 to position 327 of the structural gene, was respectively substituted with phenylalanine (F), tryptophan (W), leucine (L), and asparagine (N) codons. As regards these four phage clones, by using the other nine types of synthetic oligonucleotides, the base sequences of all of the structural genes were determined. It was demonstrated that no mutation was present except the objective mutation. These phage clones were designated as M13SfamyY83F, M13SfamyY83W, M13SfamyY83L, and M13SfamyY83N, respectively.

The base sequences, together with the amino acid sequences, are shown in SEQUENCE ID NOs:1, 3, 5, and 7, concerning the structural genes of the four types of the variant-type Sfamy enzymes. In the above base sequences, base sequences encoding for an amino acid residue, that replaced the Y83 residue, are shown.

Expression vectors for yeast were prepared as follows. First, $E.$ $coli$ MV1190 strain was separately infected with the above-mentioned four types of phage clones (M13SfamyY83F, M13SfamyY83W, M13SfamyY83L, and M13SfamyY83N). From the bacteria, each respective RF DNA was then isolated by alkaline bacteriolysis; then it was subsequently treated with restriction enzymes EcoRI and PstI, and it was subjected to agarose electrophoresis, to yield a 2.5 kb DNA fragment carrying each of the respective variant α-amylase genes. Because each of the fragments originally contained a promoter region and a terminator region essential for expression of α-amylase, each of the fragments was inserted in and ligated with the multi-cloning site of a yeast-$E.$ $coli$ shuttle vector, YEp351, which had been preliminarily digested with the same two types of restriction enzymes. The recombinant plasmids were used for transforming $E.$ $coli$ XL1-Blue strain, and from the resulting bacteria of the transformants, the plasmid DNAs were isolated by alkaline bacteriolysis. A part of each plasmid DNA was used to confirm that the objective 2.5 kb DNA fragment was inserted in the multi-cloning site. The plasmids were individually designated as pSA5Y83F, pSA5Y83W, pSA5Y83L, and pSA5Y83N.

Following the method of Hinnen et al., a baker's yeast (Saccharomyces cerevisiae) strain KK4 was transformed with 3 μg of each of these recombinant yeast expression vectors, to isolate four types of transformants (KK4:pSA5Y83F, KK4:pSA5Y83W, KK4:pSA5Y83L, and KK4:pSA5Y83N), using as the selective marker the leucine biosynthesis gene in the vectors. Wherein, the host yeast Saccharomyces cerevisiae strain KK4 was a known yeast, with a gene marker attached (α, ura 3, his ⅓, trp 1, leu 2, gal 80). Furthermore, the α-amylase gene of yeast Saccharomycopsis was inserted in the multi-cloning site of a yeast expression vector YEp351 (see Yeast, 1986, 2, 163–169), to prepare the yeast expression vector pSA5.

Transformation of the baker's yeast (by the method of Hinnen et al.) will now be explained hereinafter. The KK4 strain was cultured overnight in the YPD liquid medium at 30° C., and 3 ml of the resulting yeast in solution was inoculated and cultured in 100 ml of the YPO medium at 30° C. for several hours. When the yeast reached a logarithmic growth stage (at a Klett figure of 180 to 200), the yeast were harvested by centrifugation and washed in TE solution (40 ml), and the resulting yeast were suspended in the TE solution (6 ml). 2 ml of the suspension was transferred into an L-type test tube, followed by addition of 0.2M lithium acetate (2 ml), with subsequent shaking at 30° C. for 1 hour. Then, glycerol was added (0.7 ml), after which 90 μg of each one of the recombinant plasmid DNA was added, with stirring; then the resulting mixture was kept at 30° C. for 30 minutes. Next, 4.5 ml of 70% polyethylene glycol #4000 was added to and mixed with the mixture, and it was kept at 30° C. for 1 hour. Then, the mixture was heated at 42° C. for 5 minutes, followed by rapid cooling at room temperature. Then, 10.5 ml of water was mixed into the mixture. The yeast were harvested from the mixture with a centrifuge, washed again with 10.5 ml of water, and then were collected. Finally, the yeast were suspended in 7.5 ml of water. 0.5 ml of the suspension, containing each one of the transformed cells respectively, was mixed in 2.5 ml of 0.7% soft agar, and inoculated and cultured in a solid synthetic selective medium, containing glucose as a single carbon source but without containing leucine, at 30° C. for several days, to isolate each of the transformed baker's yeasts. As accession numbers FERM P-13494, FERM P-13493, FERM P-13492, and FERM P-13491, these transformants; i.e. KK4:pSA5Y83F, KK4:pSA5Y83W, KK4:pSASY83L, and KK4:pSA5Y83N, were deposited in the National Institute of Bioscience and Human-Technology of the Agency of Industrial Science and Technology, at 1-3, Higashi 1-chome, Tukuba-shi, Ibaraki-ken, 305, Japan. These four transformants were deposited on Mar. 2, 1993, and will have deposited to the institute for the period similar to those under the term of the Budapest treaty. All restrictions on the availability to the public of the deposited materials will be irrevocably removed upon the granting of a patent. A similar expression vector for the wild-type α-amylase (Sfamy) gene was prepared and designated as pSA5. The resulting transformant of pSA5 was designated as KK4:pSA5.

The transformant KK4:pSA5Y83F, containing the vector (pSA5Y83F) carrying the gene to replace the Y83 residue of α-amylase with F, is a variant strain of the above-mentioned KK4 strain. Similarly, KK4:pSA5Y83W carries the vector (pSA5Y83W) containing the gene to replace the Y83 residue with W; KK4:pSA5Y83L carries the vector (pSA5Y83L) containing the gene to replace the Y83 residue with L; and KK4:pSA5Y83N carries the vector (pSA5Y83N) containing the gene to replace the Y83 residue with N.

The expression and secretion of the wild-type and variant-type α-amylases will next be explained hereinbelow, along with the purification of these enzymes. The five types of transformed baker's yeasts carrying the wild-type gene or each variant-type Sfamy gene were inoculated on the YPD liquid medium (1 liter), and were shaken and cultured at 30° C. for 5 days. Subsequently, each culture supernatant was obtained by centrifugation, and then to each was added 20 g of anion exchange resin, i.e. DE52-cellulose (manufactured by Wattmann, Co.), followed by agitation at 4° C. for 1 hour. Then the resin was precipitated and the supernatant was discarded, the remaining resin was washed three times with 500 ml of 50 mM acetate buffer, pH 5.5, containing 2.5 mM calcium chloride. Then the resin was packed in a glass column, followed by elution of proteins by a linear gradient of 1M NaCl. The enzyme activity of each fraction was assayed by iodine starch reaction. To a 16-ml portion of each active fraction was added ammonium sulfate, to a final saturation degree of 80%; this was then centrifuged, to recover the precipitate. The precipitate dissolved in 1 ml of 50 mM acetate buffer (pH 5.5) was then applied to a hydrophobic chromatography column, Butyl Toyopearl 650 (manufactured by TOSO, Co.), which had previously been equilibrated with 50 mM acetate buffer saturated with 40% ammonium sulfate, followed by elution and fractionation by a linear gradient of 40% to 0% ammonium sulfate. 10 ml of each of the active fractions was concentrated by ultrafiltration, by means of a membrane, YM30 (manufactured by Amicon, Co.), to a final volume of 0.2 ml; then it was applied to a Superose 12 column (φ10×800 mm; manufactured by Pharmacia, Co.) equilibrated with 50 mM acetate buffer for gel filtration, to yield a wild-type enzyme sample or each variant-type enzyme sample. By SDS-polyacrylamide gel electrophoresis, each of these enzyme samples was at a respective single protein band; the top of the wild-type enzyme was at the same position as the top of the variant-type enzymes. Further, it was identified by Western immunoblotting with a mouse ascites antibody and $^{125}$I-protein A that the antigenicity of the wild-type enzyme agreed well with that of the variant-type enzymes. By the procedures described above, thus, the wild-type and variant-type α-amylases were thoroughly purified.

It was identified that the obtained variant-type enzymes had the physicochemical properties described above.

EXAMPLE 2

A method for preparing variant-type CGTase CGTase gene was first cloned. The chromosomal DNA from B. macerans IAM 1243 strain was treated with Sau3AI and Hind III, and linked with pBR322, which was then inserted into E. coli HB101.

The cloned strain carrying the CGTase gene was detected by iodine starch reaction on a starch-containing agar medium. As a result, a recombinant plasmid pMAC1 with a 4 kb DNA carrying the CGTase gene inserted was prepared. The pMAC1 was partially digested with Sau3AI; then it was inserted in and ligated with the BamHI site of the plasmid pHY300PLK, to prepare pMAA1. The plasmid was introduced in an α-amylase-defective B. subtilis strain 207-25, to prepare a transformant strain 207-25:pMAA1, which was tetracycline-resistant and had a halo formation potency during iodine starch reaction on starch-agar medium. Purified CGTases obtained from the culture supernatants of the B. macerans IAM 1243 strain and B. subtilis 207-25:pMAA1 were reacted with soluble starch. The resulting enzyme-reaction products were analyzed by paper chromatography. The main reaction product from the two enzyme reactions was α-cyclodextrin, and the two reactions could not be discriminated from each other with respect to their enzymatic natures. Furthermore, the base sequence of the DNA fragment inserted into the plasmid pMAA1 was determined. The base sequence of the structural gene of CGTase, which gene consisted of 2142 bp, was determined.

The resulting structural gene of CGTase was mutated by site-directed mutagenesis, to prepare a variant gene.

The variant gene was prepared by the Kunkel method.

From the plasmid pMAA1 carrying the CGTase gene, an XbaI-EcoRI fragment (2.5 kb) carrying the CGTase structural gene was inserted in and ligated with the multi-cloning site of M13 phage mp18. The M13 phage RF DNA containing the objective DNA fragment was infected in a ung⁻ *E. coli* strain CJ236. The infected bacterium was cultured in the LB medium. From the culture supernatant, the phage particle was recovered and extracted with phenol, to obtain uracil-containing single-stranded DNA (minus (−) chain).

In order to substitute the Y100 residue (codon; TAC) with tryptophan (codon; TGG), a 21-mer oligonucleotide was synthesized, in which the underlined TAC codon in the oligonucleotide sequence 5' TAT CAC GGT TAC TGG GCG AGG 3', SEQ ID NO.:18, was substituted with a codon TGG. By annealing the single-stranded DNA containing uracil with the synthetic oligonucleotide, followed by effecting the action of $T_4$ DNA polymerase and $T_4$ DNA ligase, the single strand (plus (+) chain) was repaired to prepare a double-stranded DNA (U-RF DNA). By inserting the U-RF DNA into ung⁺ *E. coli* strain (MV1190 strain), the DNA strand containing uracil was decomposed with the ung, to obtain the phage particle in replication or RF DNA from the DNA strand with the mutation introduced. Specifically, the MV 1190 strain was transformed with U-RF DNA by the calcium chloride method; then it was inoculated on the LB solid medium together with the indicator bacterium (MV1190 strain), followed by incubation overnight at 37° C. The phage particle from the developed plaques was transferred into the TE solution and was kept at 4° C. Simultaneously, four clones among them were separately infected into the MV1190 strain in respective 2-ml portions of LB liquid medium, followed by culturing at 37° C. for 7 hours. From the resulting culture liquid, each respective phage particle was recovered as the precipitate in polyethylene glycol; then it was treated with phenol, to separate the single-stranded DNA. The base sequence of this DNA was then determined, to select phage clones that had an accurately inserted mutation of TAC codon to TGG codon.

The base sequence of the variant gene was determined by the dideoxy method. 14 Types of 17-mer oligonucleotides ($Q_1$ to $Q_{14}$) were synthesized, which have complementarity with the minus (−) chain of the structural gene, and which cover the entire structural gene. Among them, an oligonucleotide $Q_3$, which was located at the 5' terminus of the mutated site (position 380 to position 381 of the base sequence of the structural gene i.e., positions 299 to 300 in SEQ ID NO.:9), and which corresponded to position 301 to position 317, i.e., positions 220 to 236 in SEQ ID NO.:9 was annealed with the previously isolated single-stranded DNA (minus (−) chain) under heating, with subsequent annealing. Using [α-$^{32}$P] dCTP and a commercially available sequencing kit, elongation, labeling, and termination reactions of the plus chain of the resulting annealed product were done at 37° C. The sample was heated at 100° C. for 2 minutes, following by rapid cooling in ice; then it was added to 8% acrylamide gel containing 8.3M urea, followed by electrophoresis in the TBE solution for 2 hours. After electrophoresis, the gel was transferred and dried on a filter, to prepare an autoradiogram to determine the base sequence. Through the above procedure, phage clones were prepared, wherein a part of the base sequence, corresponding to the tyrosine (Y) codon (TAC) at position 379 to position 381 of the structural gene, was substituted with a tryptophan codon (TGG). By using the other 13 types of synthetic oligonucleotides, the base sequences of all of the structural genes on the clones were identified. It was demonstrated that no mutation was present except the objective mutation. The phage clone was designated as M13CGTaseY100W.

The base sequence is shown in SEQUENCE ID NO.:9, concerning the structural gene of the variant-type enzyme CGTaseY100W. In the above base sequence, the base sequence encoding the W residue, i.e., TGG, replaces the base sequence encoding the Y100 residue, i.e., TAC.

Next, *E. coli* MV1190 was infected with the M13CGTaseY100W. From the infected bacteria, RF DNA was isolated by alkaline bacteriolysis; it was then treated with restriction enzymes XbaI and EcoRI, followed by agarose electrophoresis, to yield a 2.5 kb DNA fragment carrying the variant CGTase gene. Because the fragment originally contained a promoter region and a terminator region essential for CGTase expression, the fragment was inserted in and ligated with the PLK site of *B. subtilis* vector, pHY300PLK, which had been preliminarily digested with the same two types of restriction enzymes, to prepare pMAA1Y100W.

By transforming an α-amylase-defective *B. subtilis* strain 207-25 with the plasmid pMAA1Y100W and the plasmid pMAA1 carrying the wild-type CGTase gene, transformants 207-25:pMAA1 and 207-25:pMAA1Y100W were prepared. The host bacterium *B. subtilis* 207-25 strain was a known bacterium, with a gene marker attached ($m_{168}^-$, hsrM, recE4, amyE07, aroI906, leuA8, and lys-21). The CGTase gene from *B. macerance* was inserted into the multi-cloning site of a Bacillus vector pHY300PLK (Gene, 1984, 32, 129–135), to prepare a Bacillus vector pMAA1.

The bacterium Bacillus was transformed as follows. *B. subtilis* strain 207-25 was inoculated on a plate medium of Tryptose Blood agar base (TABA; manufactured by Difco, Co.) supplemented with glucose with 0.5%, followed by culturing overnight at 30° C. Young bacteria were scraped and inoculated on 10 ml of the CI medium (1.4% $K_2HPO_4$, 0.6% $KH_2PO_4$, 0.1% sodium citrate•$2H_2O$, 5 mM $MgSO_4$•$7H_2O$, 0.5% glucose, 0.02% Casamino acid (manufactured by Difco), 50 μg/ml L-tryptophan, 50 μg/ml essential amino acid, 100 μg/ml essential base), to a final absorbance (at 660 nm) of about 0.1, following by shaking and culturing at 36° C. When the bacteria reached a logarithmic growth stage, they were collected by centrifugation and were suspended in a two-fold volume of the CII medium (in which the contents of L-tryptophan, essential amino acid, and essential base were one-tenth the same contents in the CI medium, but other ingredients were identical with the CI medium), followed by shaking and culturing for another 40 minutes; then recombinant plasmid DNA was added (10 μg), and culturing was continued for another 40 minutes. Then the bacteria were harvested by centrifugation and were suspended in 1 ml of the LB medium. The suspension was inoculated on the TBAB medium supplemented with tetracycline (20 μg/ml) and 1% soluble starch, followed by overnight warming at 36° C., to prepare a tetracycline-resistant transformant (207-25:pMAA1 Y100W).

The transformant (207-25:pMAA1 Y100W), containing a vector (pMAA1 Y100W) carrying the gene substituting the Y100 residue of CGTase with W, still belonged to the 207-25 strain.

The expression and secretion of the wild-type and variant CGTases will next be explained hereinbelow, along with the purification of the enzymes. The two types of the transformants (207-25:pMAA1 and 207-25:pMAA1Y100W) carrying the wild-type CGTase gene and the variant-type CGTase gene were separately inoculated in 1 liter of the NB medium (0.8% Nutrient Broth, manufactured by Difco, Co., 0.5% glucose, 5 mM $Ca(NO_3)_2$) supplemented with 1% soluble starch, followed by shaking and culturing at 36° C. for 5 days. Subsequently, each of the culture supernatants was obtained by centrifugation, and then to each was added ammonium sulfate, to a final saturation degree of 25%, and the resulting mixture was adjusted to pH 6.5 with an aqueous sodium hydroxide solution. The solution was centrifuged and precipitates were discarded. Then, in the presence of 15% ammonium sulfate, pH 7.8, the resulting solution was heated at 70° C. for 30 minutes. Next, to the solution was added rapidly cooled corn starch suspension, followed by agitation overnight at 4° C., to adsorb the CGTase onto the corn starch particles. Then, the CGTase-starch particle complex was recovered by centrifugation at 4° C. The CGTase was released from the complex, by keeping the complex at 40° C. for 1 hour in 50 mM acetate buffer, pH 5.5, containing 2.5 mM calcium chloride. The released CGTase was dialyzed against 50 mM acetate buffer, pH 5.5, containing 25 mM calcium chloride. The solution was applied to a DE-52 cellulose column equilibrated with the same buffer, followed by elution by a linear sodium gradient (0–1M) in the same buffer. The enzyme activity of each fraction was assayed by iodine starch reaction. A 10 ml portion of each active fraction was concentrated to a final volume of 0.2 ml by ultrafiltration, by means of a membrane YM30 (manufactured by Amicon, Co.). Then it was applied to a Superose 12 column ($\phi$10×800 mm; manufactured by Pharmacia, Co.) which had been equilibrated with 50 mM acetate buffer, and gel filtration was carried out to it, to yield wild-type CGTase and variant-type CGTase. By SDS-polyacrylamide gel electrophoresis, each of these enzyme samples was at a respective unique protein band; the top of the wild-type enzyme was at the same position as the top of the variant-type enzymes. Further, it was identified that the antigenicity of the wild-type enzyme agreed well with that of the variant-type enzyme in a similar manner in Example 1.

It was also identified that the obtained variant-type enzyme had the physicochemical properties described above.

EXAMPLE 3

Effects of replacing Sfamy Y83 residue on hydrolysis activity and transglycosylation activity In 400 μl of 50 mM acetate buffer, pH 5.5, containing 2.5 mM calcium chloride, a substrate maltoheptaose ($G_7$, $2\times10^{-3}$M) was reacted with each one of the below-mentioned five enzymes at 30° C. for 60 minutes. At that time, the concentration of the wild-type enzyme and the concentrations of the variant enzymes Y83F, Y83W, Y83L, and Y83N were respectively $4\times10^{-7}$M, $8\times10^{-7}$M, $8\times10^{-7}$M, $8\times10^{-6}$M, and $8\times10^{-6}$M, in this order. From each of the mixture solutions, 100-μl samples were sequentially taken out at intervals of 10 minutes; at each removal the sample's reaction was terminated with 30 μl of glacial acetic acid, followed by inactivation of the enzymes by 5 minutes of heating at 100° C. Subsequently, each sample was concentrated and dried. Then each sample was dissolved in 5 μl of distilled water, and 2.5 μl of the resulting solution was spotted on a paper chromatography filter (size; 25×40 cm, manufactured by Wattmann, Co., 3MM), for development at 55° C. for 2 hours in a pressure-resistant vessel containing a development solvent (ethyl acetate:methanol:water=37:40:23). The development was then repeated, so that it was done twice. Subsequently, each of the filters was dried and sprayed with 10 ml of 50 mM acetate buffer, pH 5.5 containing 200 U Rhizopus glucoamylase; then the filter was kept in a sealed vessel at 55° C. for 30 minutes. Then, on the filter, spots treated with glucoamylase were detected by the silver nitrate coloring method. Coloring with silver nitrate was carried out as follows: The filter treated with glucoamylase was successively immersed in an acetone solution of silver nitrate, an alcoholic sodium hydroxide solution, and a fixing solution, in this order; and it was successively dried. The substrate and the enzymatic reaction products were assayed quantitatively, by measuring the coloring intensity of silver nitrate-colored spots on a paper chromatogram using a densitometer.

As a result, it was clearly shown that from the substrate $G_7$, transglycosylation products of longer chains: $G_{10}$, $G_{11}$, and $G_{12}$, were prepared in all cases with each variant enzyme. Table 1 shows the ratio in % (conversion ratio in %) of transglycosylation reaction products ($G_{\geq 10}$) of a longer chain than maltodecaose ($G_{10}$) to the reduction of the substrate, when 40% of the substrate $G_7$ was consumed during the individual enzymatic reactions. Compositional ratios (%) of $G_{10}$, $G_{11}$, and $G_{12}$ to the total $G_{\geq 10}$ products are also shown in Table 1.

TABLE 1

| | Rate of conversion to $G_{\geq 10}$ (%) | Composition ratio in all $G_{\geq 10}$ (%) | | |
|---|---|---|---|---|
| | | $G_{10}$ | $G_{11}$ | $G_{12}$ |
| Wild-type | 0 | — | — | — |
| Y83F | 65 | 25 | 55 | 20 |
| Y83W | 70 | 20 | 60 | 20 |
| Y83L | 50 | 25 | 55 | 20 |
| Y83N | 60 | 20 | 60 | 20 |

EXAMPLE 4

Transglycosylation activity of enzyme with Sfamy Y83 residue replaced

In order to analyze the transglycosylation activity of variant enzymes, enzyme reactions were carried out employing, as the substrate, maltopentaose with a p-nitrophenyl group introduced at its reducing end terminus ($G_5$-PNP), and the products were quantitatively analyzed by HPLC (high-performance liquid chromatography). When 50% of $G_5$-PNP was consumed, comparison was made of development patterns of reaction products produced by the wild-type enzyme and those of reaction products produced by each variant enzyme. With the wild-type enzyme, $G_5$-PNP was hydrolyzed principally into $G_3$ and $G_2$-PNP, but there were no transglycosylation reaction products larger than $G_5$-PNP. Alternatively, all of the variant enzymes produced p-nitrophenyl α-D-malto-octaoside ($G_8$-PNP), which accounted for 50% of the products in total. Compared with the wild-type enzyme, the decomposition products; i.e. $G_3$ and $G_2$-PNP, in the reaction of each variant enzyme, were decreased to 30% and 50%, respectively, of their initial amounts. This finding regarding the specific $G_3$ reduction indicates that the $G_3$ prepared through decomposition is transferred onto the non-reducing end terminus of the unreacted substrate ($G_5$-PNP), to prepare $G_8$-PNP.

The occurrence of hydrolysis versus transglycosylation reaction depends on whether water molecules or substrate molecules attack, in a nucleophilic manner, the carbonium ion intermediate as the enzyme reaction intermediate. The obtained increase in the transglycosylation activity in these variant enzymes can be explained by the reaction mechanism involving the carbonium ion intermediate. Based on the above experimental evidence, it is demonstrated by the present inventors that the phenolic OH group of the Sfamy Y83 residue has a definitely important function to provide $H_2O$ molecules to the carbonium ion intermediate. It has also been clearly shown that, in the variant enzymes, the function of the phenolic OH to provide $H_2O$ molecules is deteriorated by the substitution of the Y83 residue with another amino acid residue, so that the possibility of the otherwise unreacted substrate (in the presence of Y83 residue) attacking the carbonium ion intermediate, in a nucleophilic manner, is resultantly enhanced, to prepare transglycosylation reaction products of longer chains.

EXAMPLE 5

Hydrolysis activity of enzyme with Sfamy Y83 residue replaced

Furthermore, using a substrate with both its non-reducing end terminus and its reducing end terminus modified, i.e. 3KB-$G_5$-CNP (chloronitrophenyl maltopentaose wherein the hydroxyl group at position 3 of the glucose residue at the non-reducing end terminus is ketobutylated; manufactured by Ono Pharmaceutical Company), the hydrolysis activities of the wild-type enzyme and the variant-type enzymes were determined. The results are shown in Table 2. 3KB-$G_5$-CNP cannot function as a substrate for transglycosylation reaction because of the modification of both of the termini, and therefore, only the hydrolysis activity can be assayed.

with a freeze-dryer. The dried products were then dissolved in 10 ml of distilled water, and the resulting samples were analyzed by paper chromatography and HPLC, to determine the molecular species and sugar composition of the reaction products.

Paper chromatography was carried out as follows. An analytical sample solution (2.5 µl) was spotted on a paper chromatography paper (manufactured by Wattmann, Co., 3 MM), of size 25×40 cm, for subsequent development at 55° C. for 2 hours in a pressure-resistant vessel containing a developing solvent (ethyl acetate:methanol:water= 37:40:23). Then the development was repeated, so that it was conducted twice. Subsequently, each of the filters was dried and sprayed with 10 ml of 50 mM acetate buffer, pH 5.5, containing 200 U Rhizopus glucoamylase; then the filter was kept in a sealed vessel at 55° C. for 30 minutes. Then, on the filters, spots treated with glucoamylase were detected by the previously described silver nitrate coloring method. The enzymatic reaction products were quantitatively assayed, by measuring the coloring intensity of silver nitrate-colored spots on a paper chromatogram using a densitometer. Consequently, five types of oligosaccharides were detected in the spots of the reaction products of both of the enzymes.

By subsequently using the same method, preparative paper chromatography was carried out to prepare the five types of oligosaccharides. The each purified oligosaccharide (200 µg) resultantly obtained was separately dissolved in 20 µl of 50 mM acetate buffer, pH 5.5, followed by addition of 10 U glucoamylase; then it was kept at 50° C. for 20 minutes, followed by application to an MIC gel column (manufactured by Mitsubishi Chemicals, Co.) for liquid chromatography, to analyze the sugar composition at 65° C. The types of the transglycosylation reaction products produced by the wild-type enzyme reaction and by the variant-

TABLE 2

|  | Wild-type | Y83F | Y83W | Y83L | Y83N |
| --- | --- | --- | --- | --- | --- |
| kcat (min$^{-1}$) | $9.2 \times 10^2$ | $1.5 \times 10^2$ | $1.3 \times 10^2$ | $1.1 \times 10^1$ | $1.6 \times 10^1$ |
| Km (× 10$^{-3}$ M) | 0.06 | 0.13 | 0.15 | 0.12 | 0.19 |
| kcat/Km (min$^{-1}$ · M$^{-1}$) | $1.5 \times 10^7$ (100%) | $1.2 \times 10^6$ (8%) | $8.7 \times 10^5$ (6%) | $9.3 \times 10^4$ (1%) | $8.6 \times 10^4$ (1%) |

The results shown in Table 2 indicate that in the variant-type enzyme Y83F, in which the phenolic OH group was deleted from the Y83 residue, the hydrolysis activity (in kcat/Km) is reduced to one-tenth that of the wild-type enzyme, and that in the variant enzymes Y83L and Y83N, the activity is reduced to one-hundredth that of the wild-type enzyme. These results indicate that the phenolic OH group at the Y83 residue plays a definitely important function to provide $H_2O$ molecules to the carbonium ion intermediate.

EXAMPLE 6

Effects of replacing CGTaseY100 residue on transglycosylation activity

To each of two 100-ml portions of 50 mM acetate buffer, pH 5.5, containing 5% soluble starch and 5% sucrose, was added 700 THU (Tilden-Hudson unit) of one of wild-type CGTase and CGTaseY100W, thereby preparing respective enzyme mixtures, and reaction was allowed to proceed at 50° C. for 10 hours. Subsequently, the reaction mixtures were kept at 100° C. for 10 minutes, to inactivate each enzyme. The reaction products were concentrated and dried type enzyme reaction (CGTaseY100W enzyme reaction), as well as the compositional ratios of the products, are shown collectively in Table 3.

Table 3 shows that 50% of the initial sucrose in the CGTaseY100W enzyme reaction was utilized as the receptor in the action of transglycosylation, and that the resulting transglycosylation reaction products contained $G_2F$ (α-maltopyranoyl-β-D-fructofuranoside), $G_3F$ (α-maltotripyranoyl-β-D-fructofuranoside), and $G_{\geq 4}F$ (products of longer chains), at 21%, 12%, and 10%, respectively. In contrast, 25% of the initial sucrose in the wild-type enzyme reaction was utilized as the receptor in the action of transglycosylation, and the reaction products contained $G_2F$, $G_3F$, and $G_{\geq 4}F$ at 9%, 6%, and 5%, respectively. These results indicate that the transglycosylation activity of CGTaseY100W was greater than that of the wild-type enzyme.

TABLE 3

| | Rate of trans- glycosyla- tion* (%) | Composition of each sugar (%) | | | | |
|---|---|---|---|---|---|---|
| | | Sucrose (GF) | Maltose ($G_2$) | $G_2F$ | $G_3F$ | $G_{\geqq 4}F$ |
| Wild-type | 25 | 33 | 47 | 9 | 6 | 5 |
| Y100W | 50 | 24 | 33 | 21 | 12 | 10 |

$$*\text{Rate of transglycosylation (\%)} = \frac{\text{Amount of transferred sugar}}{\text{Total amount of sucrose and transferred-sugar}} \times 100$$

Having described our invention as related to the present embodiments, it is our intention that the invention not be limited by any of the details of the description, unless otherwise specified, but rather be construed broadly within its spirit and scope as set out in the accompanying claims.

---

What we claim is:

1. A variant carbohydrate hydrolase selected from the group consisting of α-amylase and cyclomaltodextrin glucanotransferase, wherein the tyrosine residue present in the active center of said α-amylase or said cyclomaltodextrin glucanotransferase that functions to provide $H_2O$ molecules to a reaction intermediate is substituted with another amino acid residue.

2. The variant carbohydrate hydrolase as claimed in claim 1, wherein said tyrosine residue is present within a 5 angstrom range from three catalytic acidic amino acid residues.

3. The variant α-amylase as claimed in claim 1, wherein said α-amylase is from *Saccharomycopsis fibuligera*, and wherein the tyrosine residue at position 83 of the amino acid sequence of said α-amylase is substituted with a phenylalanine residue, SEQ ID NO.:2, a tryptophan residue, SEQ ID NO.:4, a leucine residue, SEQ ID NO.:6, or an asparagine residue, SEQ ID NO.:8.

4. A variant α-amylase gene of *Saccharomycopsis fibuligera*, wherein the base sequence at positions 247 to 249 of said gene is mutated into one of TTC, SEQ ID NO.:1, TGG, SEQ ID NO.:3, CTC, SEQ ID NO.:5, or AAC, SEQ ID NO.:7.

5. The variant cyclomaltodextrin glucanotransferase as claimed in claim 1, wherein said cyclomaltodextrin glucanotransferase is from *Bacillus macerans*, and wherein the tyrosine residue at position 100 of the amino acid sequence of said cyclomaltodextrin glucanotransferase is substituted with a tryptophan residue, SEQ ID NO.:10.

6. A variant cyclomaltodextrin glucanotransferase gene of *Bacillus macerans*, wherein the base sequence at positions 299 to 300 of said gene is mutated into GG, SEQ ID NO.:9.

7. A DNA sequence, which comprises a first sequence at positions 247 to 249, of a variant α-amylase gene from *Sacchramycopsis fibuligera*, which corresponds to positions 325 to 327 of the structural α-amylase gene, said first sequence being mutated into one of TTC, SEQ ID NO.:1, TGG, SEQ ID NO.:3, CTC, SEQ ID NO.5, or AAC, SEQ ID NO.:7, or a second sequence at positions 299 to 300 of a variant cyclomaltodextrin glucanotransferase gene, from *Baccilus macerans*, which corresponds to positions 380 to 381 of the structural cyclomaltodextrin glucanotransferase gene, said second sequence being mutated into GG, SEQ ID NO.:9.

8. A vector, which comprises the DNA sequence as claimed in claim 7.

9. A transformant, which comprises the vector as claimed in claim 8.

10. A transformant, which comprises one of FERM P-13494, FERM P-13493, FERM P-13492 or FERM P-13491.

\* \* \* \* \*

UNITED STATES PATENT AND TRADEMARK OFFICE
CERTIFICATE OF CORRECTION

PATENT NO.   : 5,538,882
DATED        : July 23, 1996
INVENTOR(S)  : MATSUI et al.

It is certified that error appears in the above-indentified patent and that said Letters Patent is hereby corrected as shown below:

Column 2, Line 63, change "5" to --3--

Column 2, Line 64, change "3" to --5--

Column 11, Line 41, change "FERM P-13494, FERM P-13493, FERM P-13492" to --FERM BP-5471, FERM BP-5470, FERM BP-5469--

Column 11, Line 42, change "FERM P-13491" to --FERM BP-5468--

Column 58,
Claim 10, Lines 1-2, change "FERM P-13494" to --FERM BP-5471--

Claim 10, Line 2, change "FERM P-13493, FERM P-13492" to --FERM BP-5470, FERM BP-5469--

Claim 10, Lines 2-3, change "FERM P-13491" to --FERM BP-5468--

Signed and Sealed this

Eighth Day of April, 1997

*Attest:*

BRUCE LEHMAN

*Attesting Officer*   Commissioner of Patents and Trademarks